(12) United States Patent
Dugast-Darzacq et al.

US010071097B2

(10) Patent No.: US 10,071,097 B2
(45) Date of Patent: Sep. 11, 2018

(54) MOLECULAR TARGETS FOR THE TREATMENT OF WOUNDS, IN PARTICULAR CHRONIC WOUNDS

(71) Applicants: URGO RECHERCHE INNOVATION ET DEVELOPPEMENT, Chenove (FR); Centre National de la Recherche Scientifique—CNRS, Paris (FR); Universite Paris Diderot—Paris 7, Paris (FR); INSERM (Institut National de la Sante et de la Recherche Medicale), Paris (FR); Ecole Normale Superieure, Paris (FR)

(72) Inventors: Claire Dugast-Darzacq, Antony (FR); Maïté Noizet, Versailles (FR); Xavier Darzacq, Antony (FR); Beatrice Spiluttini Hebert, Houilles (FR)

(73) Assignees: URGO RECHERCHE INNOVATION ET DEVELOPPEMENT, Chenove (FR); CENTRE NATIONAL DE LA RECHERCHE SCIENTIFIQUE—CNRS, Paris (FR); UNIVERITÉ PARIS DIDEROT—PARIS 7, Paris (FR); INSERM (INSTITUT NATIONAL DE LA SANTÉ ET DE LA RECHERCHE MÉDICALE), Paris (FR); ECOLE NORMALE SUPERIEURE, Paris (FR)

( * ) Notice: Subject to any disclaimer, the term of this patent is extended or adjusted under 35 U.S.C. 154(b) by 0 days.

(21) Appl. No.: 14/909,669

(22) PCT Filed: Jul. 30, 2014

(86) PCT No.: PCT/EP2014/066344
§ 371 (c)(1),
(2) Date: Feb. 2, 2016

(87) PCT Pub. No.: WO2015/018699
PCT Pub. Date: Feb. 12, 2015

(65) Prior Publication Data
US 2017/0281628 A1    Oct. 5, 2017

Related U.S. Application Data

(63) Continuation of application No. PCT/IB2013/001990, filed on Aug. 5, 2013.

(51) Int. Cl.
*C12N 15/113* (2010.01)
*A61K 48/00* (2006.01)
*A61K 31/713* (2006.01)
*A61K 31/715* (2006.01)
*C07H 21/04* (2006.01)
*A61K 31/519* (2006.01)
*A61K 9/00* (2006.01)
*A61K 31/197* (2006.01)
*A61K 31/506* (2006.01)
*A61K 45/06* (2006.01)
*A61L 15/16* (2006.01)

(52) U.S. Cl.
CPC .......... *A61K 31/519* (2013.01); *A61K 9/0014* (2013.01); *A61K 31/197* (2013.01); *A61K 31/506* (2013.01); *A61K 45/06* (2013.01); *A61L 15/16* (2013.01); *C12N 15/113* (2013.01); *A61L 2300/432* (2013.01); *C12N 2310/14* (2013.01)

(58) Field of Classification Search
None
See application file for complete search history.

(56) References Cited

U.S. PATENT DOCUMENTS

2010/0003272 A1* 1/2010 Sieweke ................ C07K 14/82
424/184.1

FOREIGN PATENT DOCUMENTS

| JP | 2000510333 | 8/2000 |
|---|---|---|
| JP | 2006503006 | 1/2006 |
| WO | 2012/120269 | 9/2012 |

OTHER PUBLICATIONS

Yang et al (Hepatology 2010;51:1291-1301) (Year: 2010).*
Valcourt et al (Mol. Oncol. 1:55-71, 2007) (Year: 2007).*
Chai et al (Gut 56:621-630, 2007) (Year: 2007).*
Daniel Nowinski et al., "Analysis of Gene Expression in Fibroblasts in Response to Keratinocyte-Derived Factors In Vitro: Potential Implications for the Wound Healing Process1," J. Invest. Dermatol., 122(1):216-221 (2004) XP055111564.
International Search Report in PCT/EP2014/066344 dated Dec. 15, 2014.

(Continued)

*Primary Examiner* — Richard A Schnizer
(74) *Attorney, Agent, or Firm* — McAndrews, Held & Malloy, Ltd.

(57) ABSTRACT

The present invention relates to a therapeutic compound comprising: an agent that inhibits the activity of at least one gene selected from the group consisting of MAF, MEOX2, SIX2 and homologs thereof having at least 50% identity with said genes and/or an agent that enhances the activity of at least one gene selected from the group consisting of CREB5, E2F1, EGR2, HIC1, IRF7, JUN, MYC, SRF, STAT4, TCF4, FOXS1, GLI1, SOX9 and homologs thereof having at least 50% identity with said gene for use in the treatment of wounds, preferably chronic wounds.

12 Claims, 13 Drawing Sheets
Specification includes a Sequence Listing.

(56) References Cited

OTHER PUBLICATIONS

Kenichi Kanai et al., "SUMOylation negatively regulates transcriptional and oncogenic activities of MafA," Genes to Cells, 15(9):971-982 (2010) XP055143349.

Martin et al., "Growth factors and cutaneous wound repair," Prog. Growth Factor Res., 4(1):25-44 (1992) XP026324179.

Omoteyama et al., "Activation of connective tissue growth factor gene by the c-Maf and Lc-Maf transcription factors," Biochem. Biophys. Res. Commun., 339(4):1089-1097 (2006) XP024923977.

Serria MS et al., "Regulation and differential expression of the c-maf gene in differentiating cultured cells," Biochem. Biophys. Res. Commun., 310(2):318-326 (2003) XP004458945.

Kim et al, "Phase II Study of the MEK1/MEK2 Inhibitor Trametinib in Patients with Metastatic BRAF-Mutant Cutaneous Melanoma Previously Treated With or Without a BRAF Inhibitor", Journal of Clinical Oncology, vol. 31, No. 4, Feb. 1, 2013, 9 pages.

\* cited by examiner a)
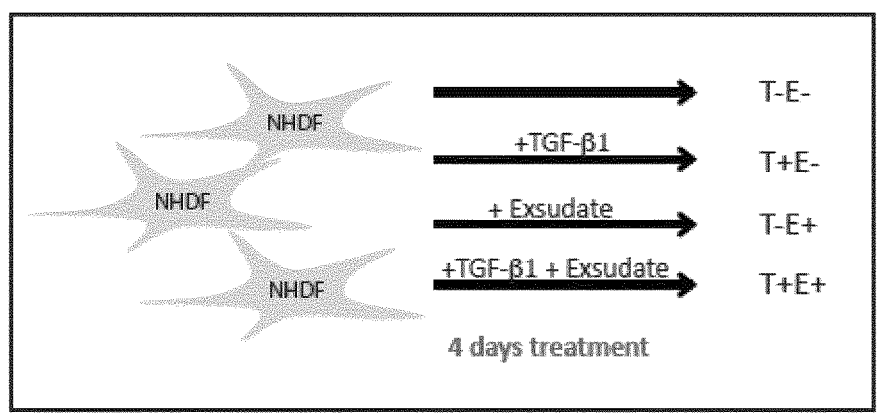
b)
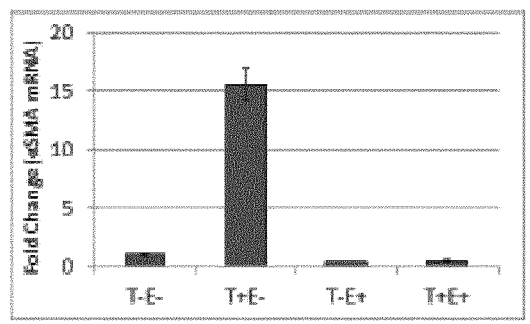
Figure 1

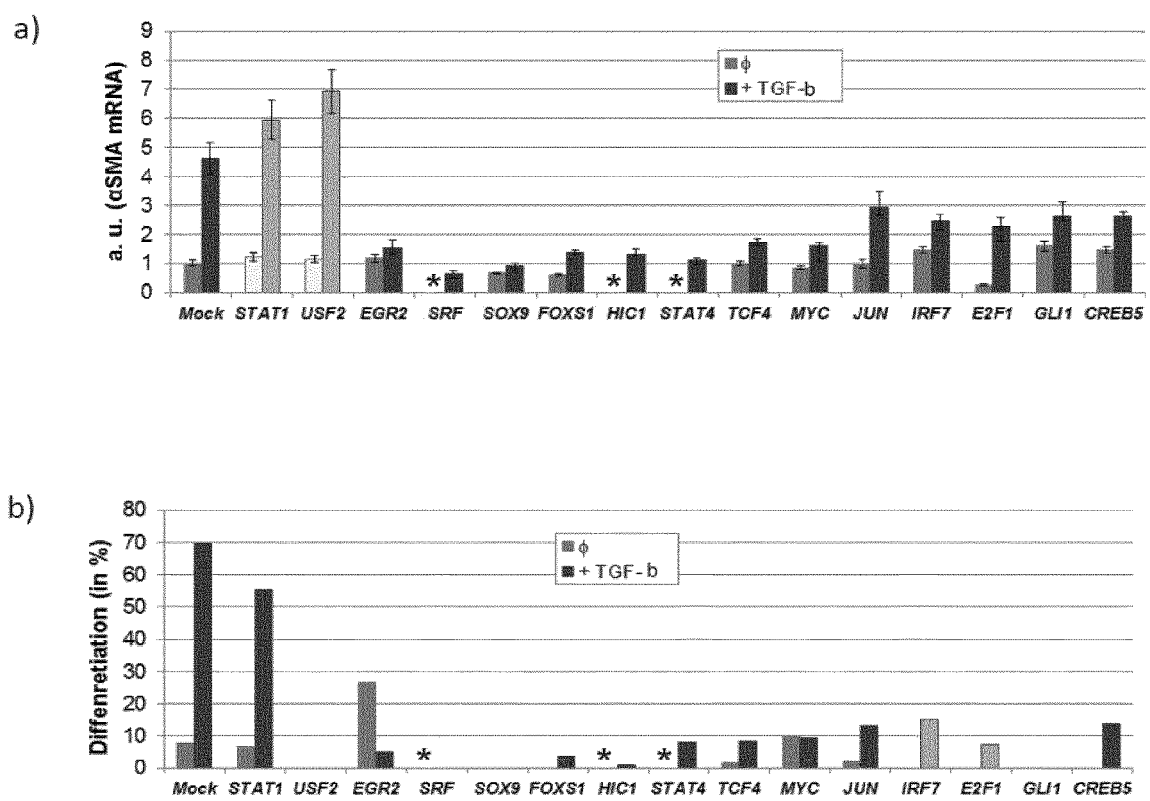
Figures 2a) and b)

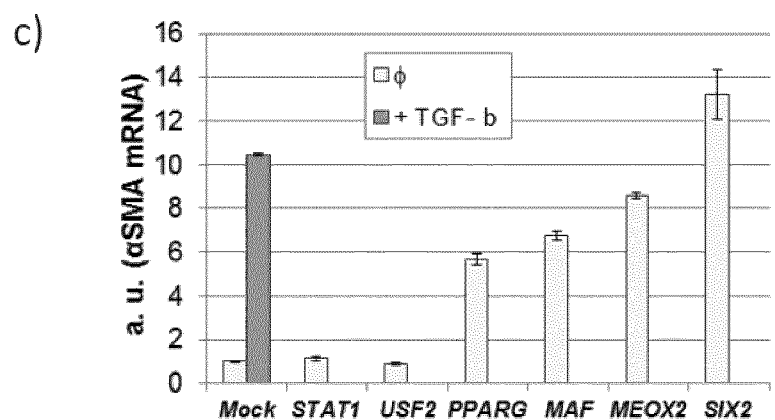
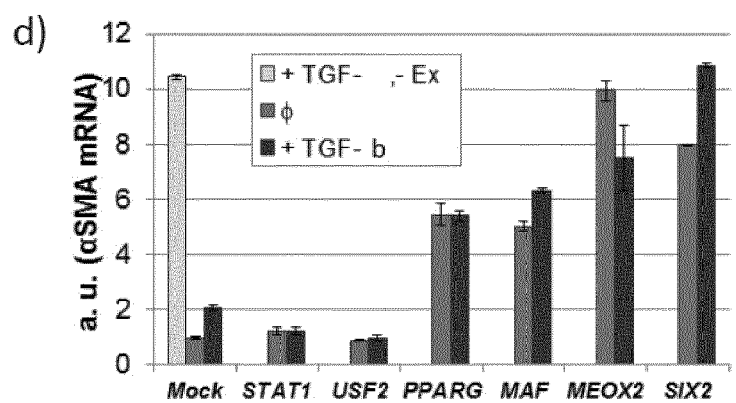
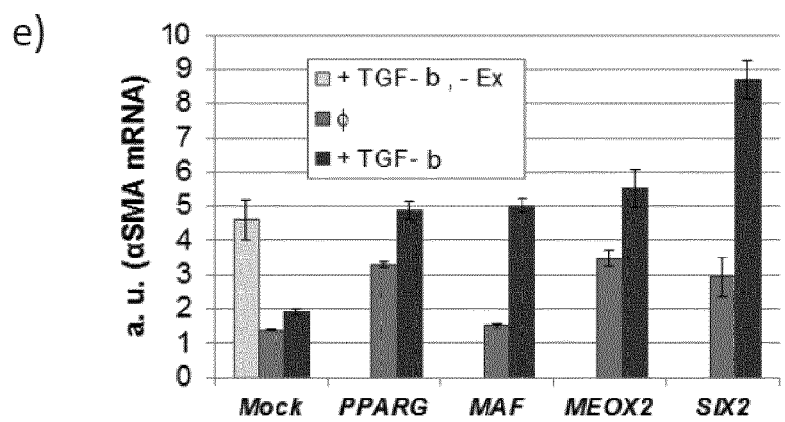
Figures 2c) 2d) and 2e)

a)
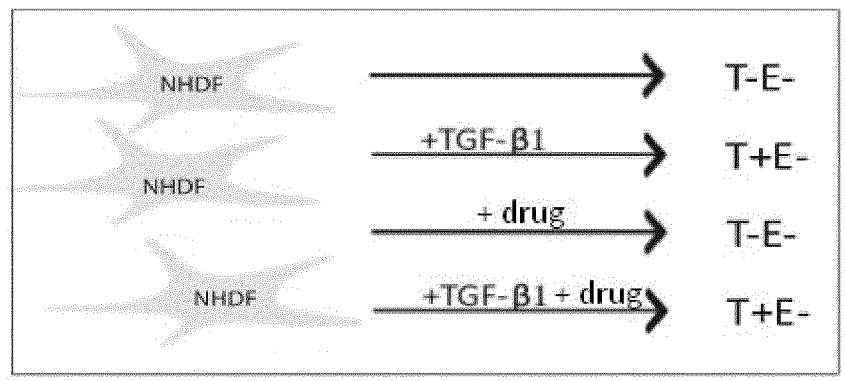
b)
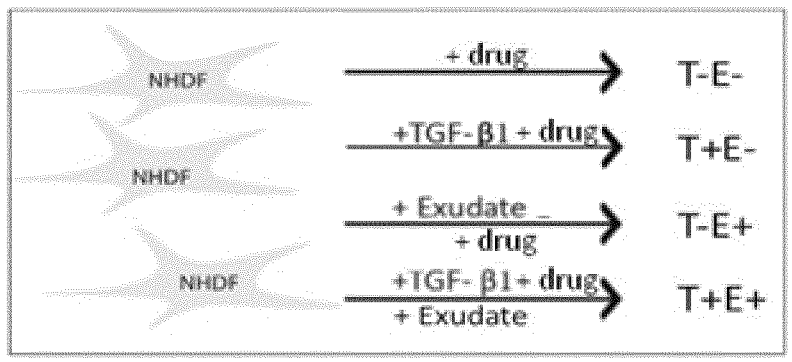
Figure 7 a)
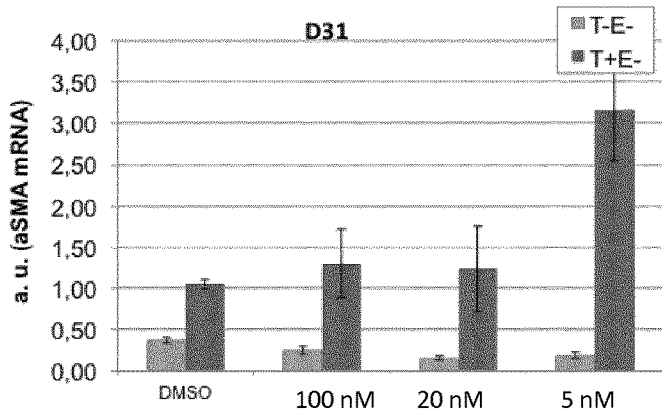
b)
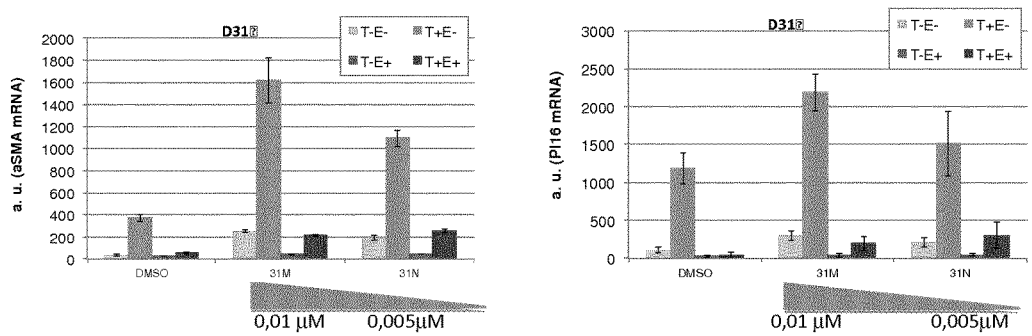
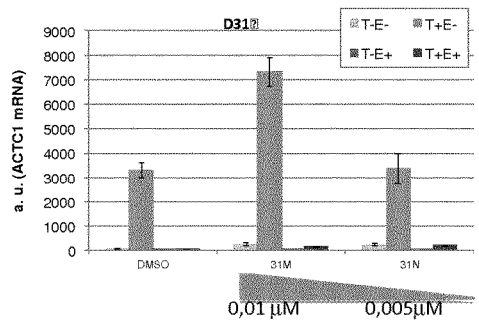
Figure 9

Figure 11

Table 1

| Symbol | Wound |
|---|---|
| CREB5 | To increase |
| E2F1 | To increase |
| EGR2 | To increase |
| ETS1 | To decrease |
| FOXS1 | To increase |
| GLI1 | To increase |
| HIC1 | To increase |
| IRF7 | To increase |
| JUN | To increase |
| MAF | To decrease |
| MEOX2 | To decrease |
| MYC | To increase |
| PPARG | To decrease |
| SIX2 | To decrease |
| SOX9 | To increase |
| SMAD3 | To increase |
| SMAD4 | To increase |
| SRF | To increase |
| STAT4 | To increase |
| TCF4 | To increase |

FIGURE 12

Table 2

| Gene | siRNA Sequence | | SEQ ID NO: |
|---|---|---|---|
| CREB5 | CCGGCGAAGGGUGGUAGACGA | Q. SI04157174 | 11 |
| | AACAGUAUUCUGUAGGAUCUA | Q. SI04141893 | 12 |
| E2F1 | UCGGAGAACUUUCAGAUCU | T, L-003259-00 | 13 |
| | GAGAAGUCACGCUAUGAGA | | 14 |
| | GAGCAGAUGGUUAUGGUGA | | 15 |
| | GAACAGGGCCACUGACUCU | | 16 |
| EGR2 | GAAGGCAUAAUCAAUAUUG | T, L-006527-00 | 17 |
| | CUACUGUGGCCGAAAGUUU | | 18 |
| | GAAACCAGACCUUCACUUA | | 19 |
| | GAGAAGAGGUCGUUGGAUC | | 20 |
| FOXS1 | AGGGCCAAUAAAGCCAUGUGA | Q. SI04152540 | 21 |
| | CUGCCCUGUAGGCUGAAGAA | Q. SI03367527 | 22 |
| GLI1 | GCAAUAGGGCUUCACAUA | T, L-003896-00 | 23 |
| | AGGCUCAGCUUGUGUGUAA | | 24 |
| | GGCGAGGGUACCUUGCAUU | | 25 |
| | CAGCUAGAGUCCAGAGGUU | | 26 |
| HIC1 | GCACAGCAACGCAACCUCA | | 27 |
| | GAGCUUCGGUGACAACCUG | | 28 |
| | UGAUCAUCGUGGUGCAGAA | | 29 |
| | GACCAUCGACCGUUUCUCU | T, L-006532-00 | 30 |
| IRF7 | GCACAAGGUGUACGCGCUC | T, L-011810-00 | 31 |
| | CAACUUCCGCUGCGCACUG | | 32 |
| | GCGCGCAUCUUCAAGGCCU | | 33 |
| | CAGGCACGGACCAGACUGA | | 34 |
| JUN | GAGCGGACCUUAUGGCUAC | T, L-003268-00 | 35 |
| | GAACAGGUGGCACAGCUUA | | 36 |
| | GAACGACCUUCUAUGACG | | 37 |
| | UGAAAGCUCAGAACUCGGA | | 38 |
| MAF | UUCGAUCUGAUGAAGUUGAA | Q. SI00076048 | 1 |
| | CCGCAGGAAUGGCAUCAGA | Q. SI03080069 | 2 |
| MEOX2 | AGCAUGCGCACUUAUGAUAUA | Q. SI04299421 | 3 |
| | CCGGCCCGUCUGUCUCUCAA | Q. SI04262174 | 4 |
| MYC | ACGGAACUCUUGUGCGUAA | T, L-003282-00 | 39 |
| | GAACACACAACGUCUUGGA | | 40 |
| | AACGUUAGCUUCACCAACA | | 41 |
| | CGAUGUUGUUUCUGUGGAA | | 42 |
| PPARγ | UCGGAGAACAAUCAGAUUGA | Q. SI03115266 | 5 |
| | GAUCAGCCAUCUUGUUCAGCAGAA | Q. SI00071873 | 6 |
| SIX2 | CAACGAGAACUCCAAUUCUAA | Q. SI00719313 | 7 |
| | CCCGGCUGAAUGGCAGCGGCAA | Q. SI04141095 | 8 |
| SMAD3 | CAACAGGAAUGCAGCAGUG | T, L-020067-00 | 43 |
| | GAGUUCGCCUUCAAUAUGA | | 44 |
| | GGACGCAGGUUCUCCAAAC | | 45 |
| | UUAGAGACAUCAAGUAUGG | | 46 |
| SMAD4 | GCAAUUGAAAGUUUGGUAA | T, L-003902-00 | 47 |
| | CCACAACCUUUAGACUGA | | 48 |
| | GAAUCCAUAUCACUACGAA | | 49 |
| | GUACAGAGUUACUACUUAG | | 50 |
| SOX9 | GGAACAACCCGUCUACACA | T, L-021507-00 | 51 |
| | GAACAAGCCGCACGUCAAG | | 52 |
| | GACCUUCGAUGUCAACGAG | | 53 |
| | GGAAGUCGGUGAAGAACGG | | 54 |
| SRF | UGAGACAGGCCAUGUGUAU | T, L-009800-00 | 55 |
| | GGACUGUGCUGAAGAGUAC | | 56 |
| | GCACCAAGAGUGAAUGAUC | | 57 |
| | GCACCAGUGUCUGCUAGUG | | 58 |
| STAT1 | GCACGAUGGGCUCAGCUUU | T, L-003543-00 | 59 |
| | CUACGAACAUGACCCUAUC | | 60 |
| | GAACCUGACUUCCAUGCGG | | 61 |
| | AGAAAGAGCUUGACAGUAA | | 62 |
| STAT4 | GAACUAAACUAUCAGGUAA | T, L-011784-00 | 63 |
| | GCAUGUAGCUGUGGUUAUU | | 64 |
| | CAAUCUAGCUACAGUGAUG | | 65 |
| | CUGCGAGACUACAAAGUUA | | 66 |
| TCF4 | GCACUUGCUUCGAUCUAUU | T, L-004864-00 | 67 |
| | GACAAAGAGCUGAGUGAUA | | 68 |
| | GCACAGCUGUUUGGUCUAG | | 69 |
| | CAACGGGACAGACAGUAUA | | 70 |
| USF2 | GCAAGACGGGAGCGAGUAA | T, L-003818-00 | 71 |
| | GGAGGGACAAGAUCAACAA | | 72 |
| | GAAGAGCCCAGCACAACGA | | 73 |
| | CAAAAUCCCUUCAGCAAUG | | 74 |

MOLECULAR TARGETS FOR THE TREATMENT OF WOUNDS, IN PARTICULAR CHRONIC WOUNDS

The present application is filed pursuant to 35 U.S.C. 371 as a U.S. National Phase application of International Patent Application No. PCT/EP2014/066344, which was filed Jul. 30, 2014, claiming the benefit of priority to International Patent Application No. PCT/IB2013/001990, which was filed on Aug. 5, 2013. The entire text of the aforementioned applications is incorporated herein by reference in its entirety.

FIELD OF THE INVENTION

The present invention relates to at least one molecular target for healing or treating wounds, in particular chronic wounds and more preferentially non healing chronic wounds. Further, the invention concerns a novel therapeutic for treating wounds and a novel gene therapy approach, involving said molecular target for treating wounds. Additionally, the invention concerns a method for treating wounds using said therapeutic or said gene therapy.

BACKGROUND OF THE INVENTION

The natural wound healing is divided into three sequential phases; each phase is characterized by specific cellular activities: the inflammatory phase, the proliferative phase and the remodeling phase.

The first phase, called the inflammatory phase, begins minutes after injury. The blood vessels rupture induces the clot formation, composed mainly of fibrin and fibronectin. The clot fills partially the lesion and allows the migration of the inflammatory cells within the lesion. The inflammatory cells are recruited to debride the wound. Platelets secrete factors, such as growth factors or cytokines, which induce the recruitment of cells implicated in the wound healing (inflammatory cells such as neutrophils and macrophages, fibroblasts and endothelial cells).

The second phase is called the proliferative phase and corresponds to the development of the granulation tissue. Fibroblasts migrate into the wound area, proliferate and form a new provisional extracellular matrix by secreting extracellular matrix (ECM) proteins. Then endothelial cells migrate to promote the neovascularization or angiogenesis of the lesion. Inside the granulation tissue, fibroblasts activate and differentiate into myofibroblasts, presenting contractile properties thanks to their expression of alpha-smooth muscle actin (similar to that in smooth muscle cells). Myofibroblasts have a key role in wound healing as they provide the contraction of the wound. Finally, keratinocytes migrate from the wound edge, proliferate and differentiate to reconstitute the epidermis.

The last phase of the wound healing process appears after the wound closure. It corresponds to the remodeling of the granulation tissue. The granulation tissue is reorganized, type III collagen is replaced by type I collagen, as normal dermis is principally composed of type I collagen. During this phase, myofibroblasts in excess are eliminated by apoptosis. The last phase of the wound healing is long. One year after injury, the scar is remodeled; it gets less red and thinner.

However, this process is not only complex but fragile; it is susceptible to interruption or failure leading to the formation of chronic or non-healing wounds or formation of abnormal scars. Factors which may contribute to this include diseases (such as diabetes, venous or arterial disease), age, infection or tissue localization.

Chronic or Non-Healing Wounds

Chronic wounds are a worldwide health problem, in part due to a lack of adequate methods of treatment. In 2010, more than 7 million people worldwide suffered from chronic wounds, and the projected annual increase is at least ten percent.

Chronic wounds are sometimes non-healing wounds. Common types of chronic wounds include, but are not limited to, venous leg ulcers, diabetic foot ulcers, decubitus ulcers, arterial leg ulcers, those of mixed etiology (venous and arterial) or those with no known etiology. We can also find acute wounds that become chronic as they do not heal correctly.

Non-healing wounds or chronic wounds are a challenge for the patient, the health care professional, and the health care system. They significantly impair the quality of life for millions of people and impart burden on society in terms of lost productivity and health care money.

Wound healing is a dynamic pathway that leads to the restoration of tissue integrity and functions. A chronic wound or non-healing wound develops when the normal reparative process is disturbed. By understanding the biology of wound healing, the physician can optimize the wound healing by choosing the adequate treatment.

In chronic or non-healing wounds, the natural healing process is altered, and thus healing is prolonged, incomplete and sometimes wounds never close. A chronic wound occurs when some factor causes the disruption of the normal inflammatory and proliferative phases. By enhancing or manipulating factors involved in wound healing it may therefore be possible to correct the process, thereby reducing the likely occurrence of a chronic wound or accelerate its subsequent repair.

Role of Fibroblasts in Wound Healing

Fibroblasts are implicated in the process of wound healing, this involves several steps of differentiation from a quiescent fibroblast to a mobilized fibroblast that will transform into a myofibroblast and finally enter apoptosis. In chronic or non-healing wounds, this process is misregulated and fibroblasts fail to undertake the myofibroblast differentiation and are found in the wound as unfunctional fibroblasts, called pseudo senescent fibroblasts (Telgenhoff D, Shroot B (2005) Cellular senescence mechanisms in chronic wound healing. Cell Death Differ 12: 695-698). The aim of the present invention is to map, at the whole genome scale, the different genes that needs to be activated or deactivated during this process, and thus facilitates the healing process of the wound.

Human fibroblasts have the ability to enter into a physiological process named senescence, which permits a limited replicative cell cycle and thus avoids loss of genetic information. It usually occurs when a cell has already conducted several rounds of replication (called replicative senescence and dependent from telomere length), but can also occur in response to environmental stress (Muller M (2009) Cellular senescence: molecular mechanisms, in vivo significance, and redox considerations. Antioxid Redox Signal 11: 59-98). Senescence cells are arrested in cell cycle but maintain metabolic activity (Telgenhoff D, Shroot B (2005) Cellular senescence mechanisms in chronic wound healing. Cell Death Differ 12: 695-698).

Fibroblasts of chronic wounds lose some of their functionalities, and more particularly, they lose part or all of their replicative function (Telgenhoff D, Shroot B (2005) Cellular senescence mechanisms in chronic wound healing. Cell Death Differ 12: 695-698). In a wound, human fibroblasts are also associated with an up-regulation of APA-1, a protein which induces matrix remodeling, demonstrating that pseudo-senescence fibroblast phenotype was not induced by telomere attrition (Benanti J A, Williams D K, Robinson K L, Ozer H L, Galloway D A (2002) Induction of extracellular matrix-remodeling genes by the senescence-associated protein APA-1. Mol Cell Biol 22: 7385-7397). Thus, senescent fibroblasts in chronic wounds would appear more particularly due to a chronic inflammation than to a telomere shortening (Telgenhoff D, Shroot B (2005) Cellular senescence mechanisms in chronic wound healing. Cell Death Differ 12: 695-698).

The present invention can improve the quality of a patient's life by treating wounds in a way that actively promotes healing.

SUMMARY OF THE INVENTION

The present invention relates to a therapeutic compound comprising:
an agent that inhibits the activity of at least one gene selected from the group consisting of MAF, MEOX2, SIX2 and homologues thereof having at least 50% identity with said genes
and/or
an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene
for use in the treatment of wounds, preferably chronic wounds.

The invention also relates to a pharmaceutical composition comprising a therapeutic compound as defined above, together with a pharmaceutically acceptable carrier.

In one aspect, the invention relates to a method for preparing a pharmaceutical composition as defined above comprising bringing said therapeutic compound in conjunction or association with a pharmaceutically or veterinary acceptable carrier or vehicle.

In another aspect, the invention relates to a method for treating a mammalian wound, wherein said method comprises: administering to said wound a therapeutic compound comprising:
an agent that inhibits the activity of at least one gene selected from the group consisting of MAF, MEOX2, SIX2 and homologues thereof having at least 50% identity with said genes
and/or
an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene The present invention also relates to a kit for treating a wound, preferably a chronic wound, wherein said kit comprises:
(a) at least one therapeutic compound or pharmaceutical composition as defined above; and
(b) at least one dressing for applying to said wound.

In yet another aspect, the invention relates to a combination therapeutic for treating a wound, preferably a chronic wound, comprising:

a) an agent that inhibits the activity of at least one gene selected from the group consisting of MAF, MEOX2, SIX2 and homologues thereof having at least 50% identity with said genes
and/or
an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene
and
b) at least one further therapeutic.

The present invention also relates to the use of
an agent that inhibits the activity of at least one gene selected from the group consisting of MAF, MEOX2, SIX2 and homologues thereof having at least 50% identity with said genes
and/or
an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene
for treating a wound, preferably a chronic wound, wherein said agent modulates fibroblast and myofibroblast differentiation and/or activity.

DETAILED DESCRIPTION OF THE INVENTION

Accordingly, in one aspect of the invention there is provided a therapeutic compound comprising:
an agent that inhibits the activity of at least one gene selected from the group consisting of MAF, MEOX2, SIX2 and homologues thereof having at least 50% identity with said genes
and/or
an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene
for use in the treatment of wounds, preferably chronic wounds.

Preferably, said agent is one which inhibits the activity of at least one gene chosen from MAF, MEOX2 and SIX2; or wherein said agent is one which enhances the activity of at least one gene chosen from SOX9 and GLI1.

In a preferred embodiment of the invention, said therapeutic composition also comprises at least:
(a)—an agent that inhibits the activity of PPARG or homologues thereof having at least 50% identity with PPARG
and/or
(b)—an agent that enhances the activity of at least one gene selected from the group consisting of SMAD3, SMAD4 and homologues thereof having at least 50% identity with said genes.

Indeed, the inventors have found that these genes were involved in the healing process and that their down-regulation or up-regulation would be useful for the treatment of wounds, in particular chronic wounds.

Thus, the invention involves a novel gene therapy approach and/or a novel protein therapy approach.

As used herein, the expression "agent that inhibits the activity of a gene" or "inhibitor" refers to an agent than can downregulate said gene. It encompasses agents that act at the level of the gene expression, as well as agents that act at the level of the protein, either by decreasing the amount of protein present in a given cell, or by inhibiting the protein's activity.

As used herein, the expression "agent that enhances the activity of a gene" or "enhancer" refers to an agent than can upregulate said gene. It encompasses agents that act at the level of the gene expression, as well as agents that act at the level of the protein, either by increasing the amount of protein present in a given cell, or by increasing the protein's activity. It also encompasses agents that act upstream or downstream of said gene or protein in a signaling pathway.

In one embodiment of the invention, the novel therapeutic comprises an inhibitor or enhancer of the gene expression, this inhibitor or enhancer can be either an anti-sense DNA or RNA, siRNA, shRNA, cDNA, TALENS or ribozymes, either naked or in the form of plasmid and viral vectors or a drug.

In a preferred embodiment, said therapeutic compound is a siRNA selected from the group consisting of siRNA having the sequence as set forth in SEQ ID No:1 to SEQ ID No:8 and mixtures thereof.

Typically, the expression of the MAF gene can be inhibited by the siRNAs having the sequences as set forth in SEQ ID No:1 and/or SEQ ID No:2.

```
SEQ ID NO: 1:    5'-UUCGAUCUGAUGAAGUUUGAA

SEQ ID NO: 2:    5'-CGGCAGGAGAAUGGCAUCAGA
```

Typically, the expression of the MEOX2 gene can be inhibited by the siRNAs having the sequences as set forth in SEQ ID No:3 and/or SEQ ID No:4.

```
SEQ ID NO: 3:    5'-AGCAUGCGCACUUAUGAUAUA

SEQ ID NO: 4:    5'-CCCGCCCGUCCUGUGCUCCAA
```

Typically, the expression of the PPARG gene can be inhibited by the siRNAs having the sequences as set forth in SEQ ID No:5 and/or SEQ ID No:6.

```
SEQ ID NO: 5:    5'-UCCGGAGAACAAUCAGAUUGA

SEQ ID NO: 6:    5'-GAGGGCGAUCUUGACAGGAAA
```

Typically, the expression of the SIX2 gene can be inhibited by the siRNAs having the sequences as set forth in SEQ ID No:7 and/or SEQ ID No:8.

```
SEQ ID NO: 7:    5'-CAACGAGAACUCCAAUUCUAA

SEQ ID NO: 8:    5'-CCCGCUGAAUGGCAGCGGCAA
```

In one embodiment, the agent that enhances the activity of a gene is a cDNA.

Typically, the expression of the CREB5 gene can be enhanced by administering the CREB5 cDNA.

The same applies mutatis mutandis for all the other genes listed.

The cDNA can be administered or delivered to the wound to be treated in any suitable form known to the skilled person in art. It can be delivered as naked DNA, using plasmid vectors, viral vectors, or any other suitable means.

In another embodiment, the novel therapeutic comprises an inhibitor or enhancer of the protein encoded by the gene function, this inhibitor or enhancer can be either a binding agent that binds, either reversibly or irreversibly, to inhibit or enhance protein function such as an antibody or a known, or synthesized, protein agonist or antagonist; or an agent that works upstream or downstream of the protein signaling mechanism to inhibit or enhance the protein signaling and so negate or enhance the effects of expression of the protein in wound tissue.

Said agent (inhibitor or enhancer) can be any agent known in the art to act upon a given molecular target.

Preferably, said agent is a small molecule.

Preferably, the activity of the MAF protein is targeted for its inhibition. More preferably, the MAF protein is inhibited by an antagonist of MAF, like trametinib. Trametinib is a chemical molecule commercialized by GlaxoSmithKline under the name Mekinist®.

Preferably, in another embodiment, the activity of GLI1 protein is targeted for its activation. More preferably, an agonist of GLI1 is used, more preferably Gant 61. Said compound is also known as 2,2'-[[Dihydro-2-(4-pyridinyl)-1,3(2H,4H)-pyrimidinediyl]bis(methylene)]bis[N,N-dimethylbenzenamine. In another embodiment, preferably, the activity of SOX9 protein is targeted for its activation. More preferably, an agonist of SOX9 is used, more preferably AM580. Said compound is also known as 4-[(5,6,7,8-Tetrahydro-5,5,8,8-tetramethyl-2-naphthalenyl)carboxamido]benzoic acid.

Typically, the enhancer of PPARG can be selected in the group consisting of thiazolidinediones, such as rosiglitazone and pioglitazone (Curr Drug Targets Cardiovasc Haematol Disord. 2005 October; 5(5):377-86. Role of PPAR-gamma agonist thiazolidinediones in treatment of pre-diabetic and diabetic individuals: a cardiovascular perspective. Dumasia R, Eagle K A, Kline-Rogers E, May N, Cho L, Mukherjee D).

Typically, the inhibitor of PPARG can be G3335 (CAS 36099-95-3) (Chembiochem. 2006 January; 7(1):74-82. The dipeptide H-Trp-Glu-OH shows highly antagonistic activity against PPARgamma: bioassay with molecular modeling simulation. Ye F, Zhang Z S, Luo H B, Shen J H, Chen K X, Shen X, Jiang H L.).

The therapeutic of the invention is for use in treating wounds, more ideally in chronic wounds, preferentially in non-healing wounds. These wounds are preferentially mammalian wounds, more preferentially human wounds. Chronic wounds that are preferably treated using the invention are leg ulcers, diabetic foot ulcers, pressure ulcers.

An antibody for use in the invention is most ideally a monoclonal antibody or a humanized antibody.

In the above aspects and embodiments of the invention the therapeutic is formulated for topical application, but it can also be formulated for oral, cutaneous, transcutaneous, transdermal, intravenous or any application known.

Alternatively, in the above aspects of the invention the therapeutic is formulated for application into a dressing or impregnation of a dressing.

The therapeutic of the invention may be administered with another active agent. Such active agent may be an antibiotic or antibacterial agent, an antiseptic, an antiviral, an antifungal, an analgesic, an anti-inflammatory agent, a wound healing agent, a keratolytic agent, an anesthetic agent. Such actives are well known to skilled practitioners.

In another aspect of the invention, there is provided a pharmaceutical composition for use in treating wounds comprising a therapeutic of the invention together with a pharmaceutical acceptable carrier.

Other active materials may also be present in the pharmaceutical composition, as may be considered appropriate or advisable for the wound being treated.

The carrier, or, if more than one be present, each of the carriers, must be acceptable in the sense of being compatible with the other ingredients of the formulation and not deleterious to the recipient.

The formulations include those suitable for topical, oral, rectal, nasal or any administration known and may be prepared by any methods well known in the art of pharmacy.

The composition may be prepared by bringing into association the therapeutic of the invention and the carrier. In general, the formulations are prepared by uniformly and intimately bringing into association the active agent with liquid carriers or finely bringing into association the active with liquid carriers or finely divided solid carriers or both, and then if necessary shaping the product. The invention extends to methods for preparing a pharmaceutical composition comprising bringing a therapeutic of the invention in conjugation or association with a pharmaceutically acceptable carrier or vehicle.

For topical application to the skin, compounds of conventional use may be made up into a cream, ointment, gel, jelly, solution or suspension etc. Cream or ointment formulations that may be used for the composition are conventional formulations well known in the art.

Formulations for oral administration in the present invention may be presented as: capsules, sachets or tablets each containing a predetermined amount of the active agent; as a powder or granules; as a solution or a suspension of the active agent in an aqueous liquid or a nonaqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

Additionally, or alternatively, the further aspect of the invention also, or alternatively, comprises a novel method for treating a mammalian wound, typically a chronic wound, which method comprises administering to said wound an agent that inhibits the activity of at least one gene selected from the group consisting of MEOX2, MAF, SIX2 and homologues thereof having at least 50% identity with said genes and/or an agent that enhances the activity of at least one gene selected from the group consisting of CREB5, E2F1, EGR2, HIC1, IRF7, JUN, MYC, SRF, STAT4, TCF4, FOXS1, GLI1, SOX9, preferentially FOXS1, EGR2, SOX9, TCF4, STAT4 and homologues thereof having at least 50% identity with said gene.

The invention also comprises a novel method for treating a mammalian wound, typically a chronic wound, which method further comprises administering to said wound an agent that inhibits the activity of PPARG or homologues thereof having at least 50% identity with PPARG and/or an agent that enhances the activity of at least one gene selected from the group consisting of SMAD3, SMAD4 and homologues thereof having at least 50% identity with said genes.

According to yet a further aspect of the invention there is provided a kit for treating a wound, preferably a chronic wound, wherein said kit comprises:

(a) at least one therapeutic as above described; and (b) at least one medical device for applying to said wound The term "medical device" includes an instrument, apparatus, implant, in vitro reagent, or similar or related article that is used to diagnose, prevent, or treat disease or other conditions, and does not achieve its purposes through chemical action within or on the body (which would make it a drug). Whereas medicinal products (also called pharmaceuticals) achieve their principal action by pharmacological, metabolic or immunological means, medical devices act by other means like physical, mechanical, or thermal means.

According to a yet further aspect of the invention there is provided a combination therapeutic for treating a wound comprising an inhibitor of MEOX2, MAF, SIX2 or enhancer of CREB5, E2F1, EGR2, HIC1, IRF7, JUN, MYC, SRF, STAT4, TCF4, SOX9, GLI1, FOXS1 preferentially FOXS1, EGR2, SOX9, TCF4, STAT4 gene expression and an inhibitor of MEOX2, MAF, SIX2 or enhancer of CREB5, E2F1, EGR2, HIC1, IRF7, JUN, MYC, SRF, STAT4, TCF4, SOX9, GLI1, FOXS1, preferentially FOXS1, EGR2, SOX9, TCF4, STAT4 protein activity.

The invention also comprises a combination therapeutic for treating a wound, which combination therapeutic further comprises an inhibitor of PPARG gene expression or enhancer of SMAD3, SMAD4 gene expression and an inhibitor of PPARG or enhancer of SMAD3, SMAD4 protein activity.

According to a further aspect of the invention there is provided a therapeutic for treating a wound comprising an inhibitor of MEOX2, MAF, PPARG, SIX2 protein, or a homologue thereof or an enhancer of CREB5, E2F1, EGR2, HIC1, IRF7, JUN, MYC, SMAD3, SMAD4, SRF, STAT4, TCF4, SOX9, GLI1, FOXS1, preferentially FOXS1, EGR2, SOX9, TCF4, STAT4 protein, or a homologue thereof.

The invention also comprises a therapeutic for treating a wound further comprising an inhibitor of PPARG protein, or a homologue thereof or an enhancer of SMAD3, SMAD4 protein, or a homologue thereof.

According to a further aspect of the invention there is provided use of an inhibitor of MEOX2, MAF, SIX2 protein, or a homologue thereof, in the manufacture of a medicament for treating a wound. According to a further aspect of the invention there is provided use of an inhibitor of MEOX2, MAF, SIX2, or a homologue thereof, for treating a wound.

The invention further provides use of an inhibitor of PPARG protein, or a homologue thereof, in the manufacture of a medicament for treating a wound. According to a further aspect of the invention there is provided use of an inhibitor of PPARG or a homologue thereof, for treating a wound.

The term "homologue" as used herein refers to amino acid sequences which have a sequence at least 50% homologous to the amino acid sequence of MEOX2, MAF, PPARG, SIX2 and which retain the biological activity of the MEOX2, MAF, PPARG, SIX2 sequence. It is preferred that homologues are at least 75% homologous to the MEOX2, ETS1, MAF, PPARG, SIX2 peptide sequence and, in increasing order of preference, at least 80%, 85%, 90%, 95% or 99% homologous to the MEOX2, MAF, PPARG, SIX2 peptide sequence.

According to a further aspect of the invention there is provided use of an enhancer of CREB5, E2F1, EGR2, HIC1, IRF7, JUN, MYC, SRF, STAT4, TCF4, SOX9, GLI1, FOXS1, preferentially FOXS1, EGR2, SOX9, TCF4, STAT4 protein, or a homologue thereof, in the manufacture of a medicament for treating a wound.

According to a further aspect of the invention there is provided use of an enhancer of SMAD3, SMAD4, or a homologue thereof, for treating a wound.

The term "homologue" as used herein refers to amino acid sequences which have a sequence at least 50% homologous to the amino acid sequence of CREB5, E2F1, EGR2, HIC1, IRF7, JUN, MYC, SMAD3, SMAD4, SRF, STAT4, TCF4, SOX9, GLI1, FOXS1 and which retain the biological activity of the CREB5, E2F1, EGR2, HIC1, IRF7, JUN, MYC, SMAD3, SMAD4, SRF, STAT4, TCF4, SOX9, GLI1, FOXS1 sequence. It is preferred that homologues are at least 75% homologous to the CREB5, E2F1, EGR2, HIC1, IRF7, JUN, MYC, SMAD3, SMAD4, SRF, STAT4, TCF4, SOX9, GLI1, FOXS1 peptide sequence and, in increasing order of preference, at least 80%, 85%, 90%, 95% or 99% homologous to the CREB5, E2F1, EGR2, HIC1, IRF7, JUN, MYC, SMAD3, SMAD4, SRF, STAT4, TCF4 SOX9 GLI1, FOXS1 peptide sequence.

Treatment of a wound described herein includes reference to human or veterinary use.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE FIGURES

The full identity of the genes according to the invention is available on the NCBI database, or is well known to those skilled in the art.

The legends of the figures are the following:

FIG. 1a: Schematic representation of the different treatments applied to the Normal Human Dermal Fibroblast (NHDF)

FIG. 1b: Graphic representation of the αSMA mRNA levels as assessed by RT-qPCR with the different treatments FIG. 2a: Graphic representation of the αSMA mRNA levels as assessed by RT-qPCR. NHDFs were treated either with mock siRNA or siRNA directed against different mRNA (EGR2, SRF, HIC1, STAT4, TCF4, GLI1, JUN, IRF7, E2F1, MYC, CREB5, FOXS1, SOX9 or STAT1) and concomitantly subjected or not to TGFβ1 treatment. The RTqPCR were normalized with TUBB and the mock siRNA treated (T–E–) condition was set to one. The treatments of NHDFs with siRNA against SRF, HIC1 or STAT4 lead to extensive cell death (*): no analysis was possible.

FIG. 2b: Graphic representation of the percentage of differentiated cells as assessed by the percentage of alpha SMA positive cells after treatment of NHDFs as described in a). The treatments of NHDFs with siRNA against SRF, HIC1 or STAT4 lead to extensive cell death (*): no analysis was possible.

FIG. 2c: Graphic representation of the αSMA mRNA levels as assessed by RT-qPCR. Primary human dermal fibroblasts were treated either with mock siRNA or siRNA directed against different mRNA (PPARG, MAF, MEOX2, SIX2, STAT1 or USF2). The RTqPCR were normalized with TUBB and the mock siRNA treated (T–E–) condition was set to 1.

FIG. 2d: Graphic representation of the αSMA mRNA levels as assessed by RT-qPCR. NHDFs were treated either with mock siRNA or siRNA directed against different mRNA (PPARG, MAF, MEOX2, SIX2, STAT1 or USF2) and concomitantly treated either with CWF1 alone or in combination with TGFβ1. The RT-qPCR were normalized with TUBB and to the mock siRNA treated (T–E–) condition (set to 1 but not represented on this graph). To help in analyzing the effect of the different siRNA, the condition where the cells were treated with mock siRNA and TGFβ1 is added and represents the normal differentiation (light grey bar in the mock histogram).

FIG. 2e: Graphic representation of the αSMA mRNA levels as assessed by RT-qPCR. NHDFs were treated as depicted in d) except for the exudate treatment which was performed with a different exudate from a different patient suffering from chronic wound (CWF2).

FIG. 7: Schematic representation of the different treatments with drugs applied to the Normal Human Dermal Fibroblast (NHDF) with exsudates (a) or not (b).

FIG. 9a: Graphic representation of the αSMA mRNA levels as assessed by RT-qPCR of NHDFs treated by Am580.

FIG. 9b: Graphic representation of the αSMA, PI16 and ACTC1 mRNA levels as assessed by RT-qPCR of NHDFs treated by Am580 in the presence of exsudates.

FIG. 11 provides Table 1: identifying genes to be increased or decreased in order to treat wounds, non-healing or chronic wounds.

FIG. 12 provides Table 2: siRNA sequences for each target gene.

EXAMPLE

Figure 3:
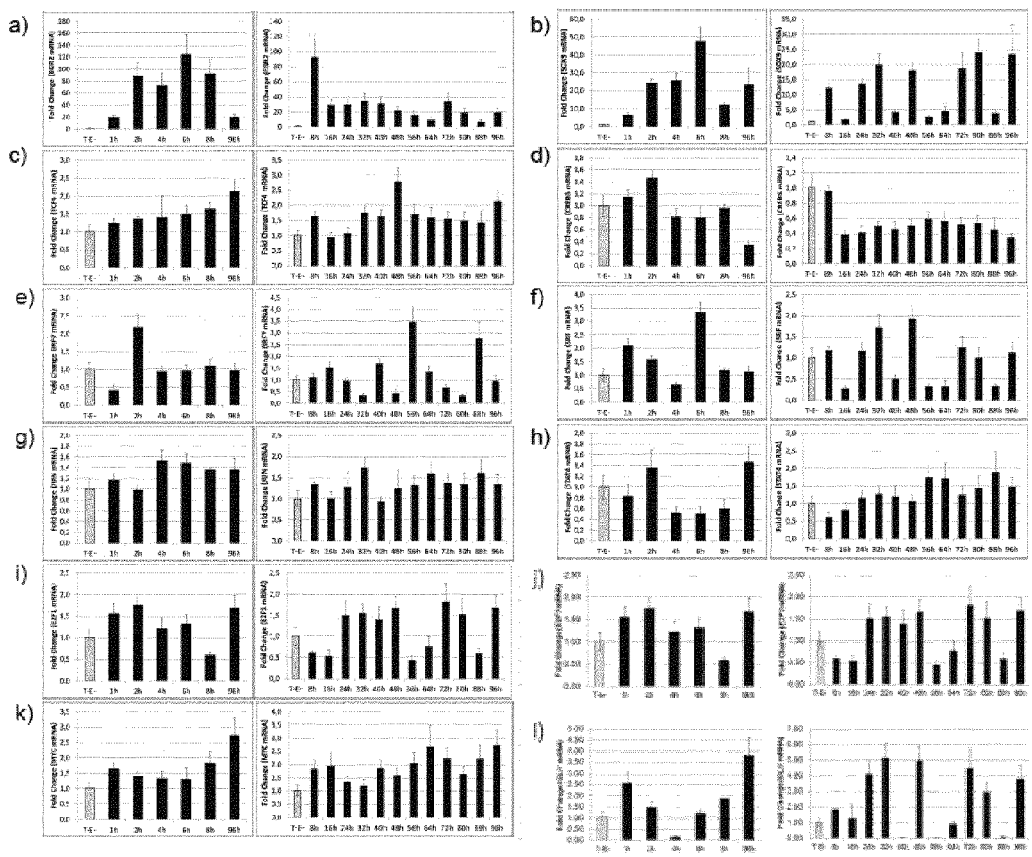
FIG. 3: short and long timing after TGFβ1 treatment for EGR2, FOXS1, SOX9, SRF, STAT4, TCF4, MYC, JUN, IRF7, E2F1, CREB5 and GLI1. For each Factor, graphic representation of the mRNA levels after increasing time of treatment of the NHDF with TGFβ as assessed by RT-qPCR.
Figure 4:
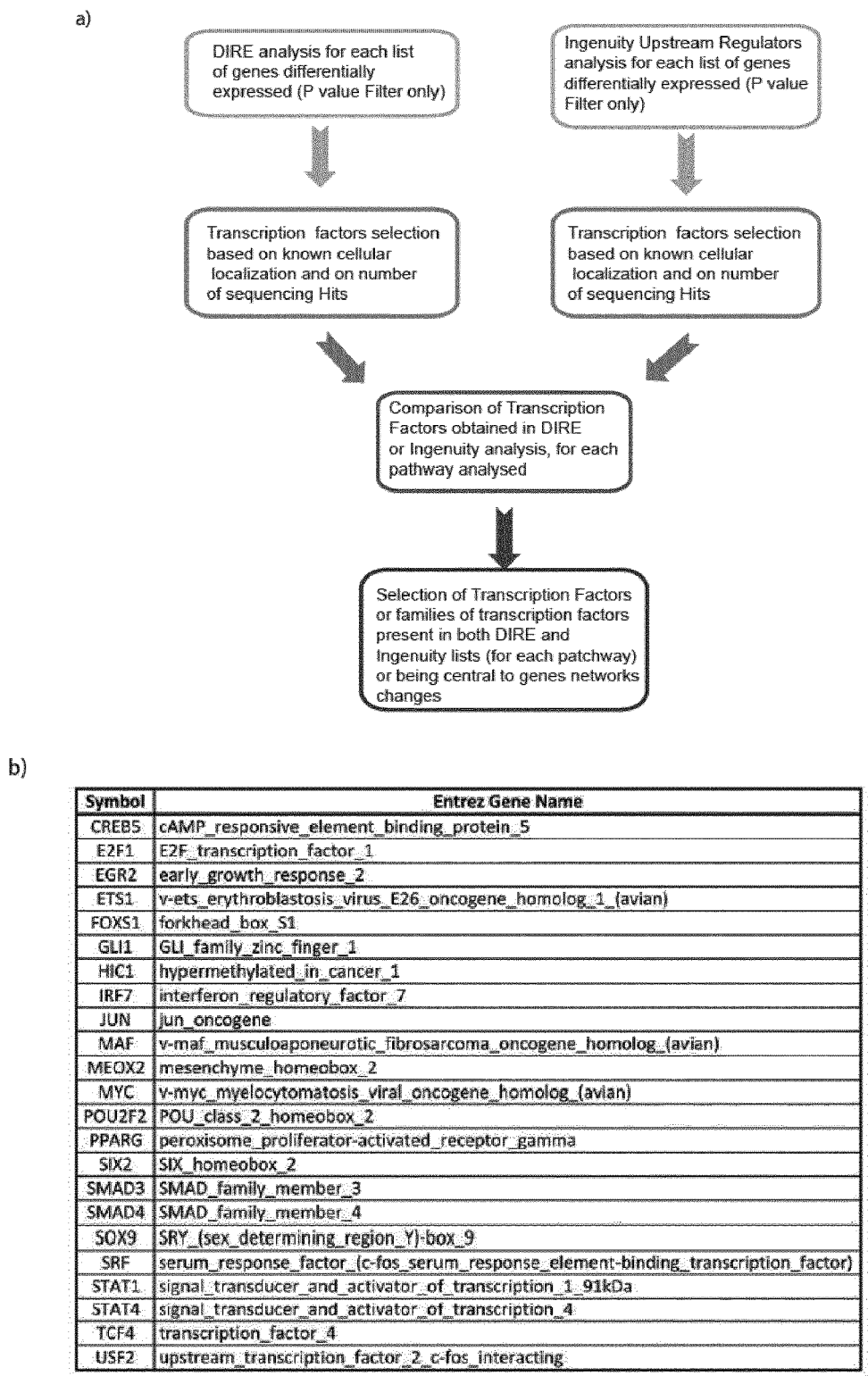
FIG. 4: Key transcription factors in fibroblast to myofibroblast differentiation
a) Graphical explanation of the in silico gene network analysis
b) Table representing the different transcription factors identified by bioinformatical and network analysis.

In response to a lesion, fibroblasts migrate into the wound where they differentiate into contractile myofibroblasts that will finally enter into apoptosis during the remodeling phase. This differentiation process can be studied ex-vivo in environmentally controlled tissue culture conditions, and therefore the timely controlled succession of different gene expression patterns can be addressed.

Materials and Methods
Establishment of an Ex Vivo Model of Chronic Wounds
Normal Dermal Fibroblast Cell Culture and Exudate Collection NHDF, isolated from human explants, were purchased from Promocell. NHDF were cultivated in DMEM-F12 (Invitrogen), supplemented with 10% FCS (Invitrogen, 5 µg/mL of insulin and 1 ng/mL of b-FGF (PromoKine)).

To collect exudates, two patients with mixed ulcers were recruited. For patient selection, it was decided to exclude any other comorbidity factor potentially involved in wound etiology: diabetes, peripheral arterial diseases, malnutrition. Exudates were collected from negative pressure therapy. All the exudates were centrifuged at 1,500×g for 3 minutes to remove cell debris. The supernatant was filtered and stored at −80° C. until use. Aliquots were used to determine protein concentration according to BCA method (Sigma).

Establishment of an Ex Vivo Model of Chronic Wounds

For experiments, cells were deprived of insulin and b-FGF during 48 hours. Then, the cells were cultivated on collagen coated culture plates in DMEM-F12, supplemented with 10% FCS, 10 ng/mL of TGF-β1 (Promocell) for 4 days. Four points were tested in order to appreciate the effect of exudate on fibroblast differentiation: untreated cells (T−E−), fibroblasts treated with TGF-β1 (T+E−), cells treated with exudate (T−E+) and finally fibroblasts treated with TGF-β1 and exudate at the same time (T+E+).

The efficiency of fibroblast differentiation was estimated by analyzing the expression of the myofibroblast marker alpha smooth muscle actin (αSMA).

Western Blotting Assay

Total proteins were extracted by scratching the cells with lysis buffer (TRIS, NaCl, NP40, EDTA, IMDTT) and incubated 30 min in ice. To remove cell debris, the samples were centrifuged at 13,000×g for 10 min at 4° C. and stored at −20° C. until use. Protein concentration was determined according to BCA method (Sigma). Equal amounts of total protein (20 µg) were loaded to NuPAGE 10% BIS-Tris gel (Invitrogen), separated by migration at 150 V, and transferred to nitrocellulose membrane (Whatman) 1 hour at 30 V. Then, membranes were stained for αSMA (Abcam) and tubulin (Abcam). Incubations were followed by secondary antibodies goat anti-rabbit IgG and goat anti-mouse IgG, respectively, conjugated with horseradish-peroxidase (HRP) (Promega). Signals were detected by ECL chemiluminescence using UptiLight HS WB Substrate (Uptima, Interchim). Bands were digitized with a scanner and the ratio between all bands density of the same blot was calculated by software (ImageJ 1.43u, 64-bit). Relative αSMA expression was normalized to the respective value for tubulin.

Total RNA Sample Preparation

After four days of experiment, treated fibroblasts were lysed with TRIzol Reagent (Invitrogen) and stored at −80° C. Then RNA was purified using chloroform and precipitated by isopropanol. Total RNA was quantified on the NanoDrop 2000c Spectrophotometer (Thermo Scientific). Reverse transcription of 500 ng total RNA to cDNA was done with oligot dT (Invitrogen) using SuperScript III RT (Invitrogen) and RNAse OUT (Invitrogen). The cDNA was store at −20° C.

Quantitative Real-Time RT-PCR

Quantitative real-time PCR (RT-qPCR) was done using 5 µL of 1:20 diluted cDNA on the LightCycler480 system (Roche) using Maxima SYBR Green qPCR Master Mix (Fermentas). Forward and reverse primers for αSMA were designed by Eurofins (MWG, αSMA forward: CTGTTTTC-CCATCCATTGTG (SEQ ID NO:9), αSMA reverse: CCAT-GTTCTATCGGGTACTT (SEQ ID NO:10)) and a 100 µM stock was stored at −20° C. Forward and reverse primer pairs were used for each RT-qPCR reaction. The cycling conditions were as follows: an initial 95° C. for 10 minutes, followed by 45 cycles of 95° C. for 15 sec, 58° C. for 30 sec, 72° C. for 20 sec. LightCycler 480 SW 1.5 was used to evaluate the TM curves, to determine the Cp and to approximate the relative concentration for each amplification reaction.

siRNA Treatment
α-Smooth Muscle Actin Immunofluorescence

Cells grown in collagen coated culture dishes, and treated as previously described, were fixed with 4% paraformaldehyde (PFA) in PBS for 15 minutes and permeabilized with 2.5% Triton X-100 (Euromedex, 2000-B) in PBS for 3 minutes. After saturation with 5% BSA in PBS, cells were stained for α-SMA (Abcam, ab5694) and for DNA (DAPI). As secondary antibody, CyTM3 conjugated anti rabbit (GE Healthcare, PA43004) was used. Samples were observed with an oil immersion objective (Plan Fluor 40X/1.30 Oil, Nikon) on a Nikon ECLIPSE Ti (Nikon). Digital images were taken with a digital camera (Cool SNAP HQ$^2$, Photometrics) and software (MetaMorf 7.5.4.0). To estimate the percentage of fibroblast differentiation due to the different treatments, the total number of cells per field was determined by the DAPI, and myofibroblasts, differentiated fibroblasts, were counted using the α-SMA staining. Then, STUDENT (t-) and $\chi^2$ tests were realized to evaluate the differentially expression of αSMA between the untreated fibroblasts (T−E−) and the treated ones.

mRNA Expression Analysis
Total RNA Sample Preparation and cDNA Synthesis

After four days of experiment, treated fibroblasts were detached with TRIzol Reagent (Invitrogen (Life Technologies), 15596-018) and stored at −80° C. Then RNA was purified using chloroform and precipitate by isopropanol. Total RNA was quantified on the NanoDrop 2000c Spectrophotometer (Thermo Scientific) and their quality was evaluated on the RNA Nano Chips (Agilent 2100 bioanalyzer, Agilent, 5067-1511). Reverse transcription of 500 ng total RNA to cDNA was done with oligot dT (Invitrogen (Life technologies), 18418-020) using SuperScript III RT (Invitrogen (Life technologies), 18080-085) and RNAse OUT (Invitrogen (Life technologies), 10777-019). The cDNA was stored at −20° C. Only samples with a good bioanalyzer profile were used for qPCR analysis.

Network Analysis

In order to enlighten master regulators of fibroblast fate after each different treatment, the inventors performed a gene network analysis treating gene expression lists determined after mRNA seq deep sequencing analysis of the gene profile of T−E− with the gene profile of T+E, T+E+ and T−E+1. In these analysis and based on the assumption that the decrease or increase of interconnected genes is of stronger significance than a significant Log FC, the inventors have used lists of genes selected only based on their P value and not on the value of their Log FC. The inventors have performed two types of analysis: an ingenuity "upstream regulator analysis" and a DIRE analysis. The Ingenuity "upstream regulator analysis", given the particular profile of genes expression between two conditions, consists in selecting potential upstream regulators. The DIRE analysis is based on the selection of potential common regulatory elements between genes based on these elements conservation during evolution. From these identified elements, DIRE is able to provide a list of master regulators for a list of co-regulated genes. From those two analyses, and for each list analyzed, the inventors have selected Transcription Factors (TFs) expressed in at least one of the two conditions considered in the concerned list (i.e. number of sequencing his superior to twenty in at least one of the two conditions). Then, the inventors have deeply compared the two sets of analysis and decided to keep in the "key regulators lists" transcription factors belonging to both analyses. Because of possible bias in these two analyses the inventors also decided to rescue transcription factors belonging only to one analysis and not the other but presenting very interesting target genes pattern in one list or the other. Altogether, these genes networks analysis allowed proposing a list of TFs being key regulators in one or the other fibroblast fate.

For the chronic or non-healing wound model, chronic wound exudates were added to cell cultures (500 µg/mL of total proteins of exudate). The experiments that were performed are depicted in FIG. 1a): cells were either not treated (T−E−), either treated with TGFβ alone (T+E−), exudate alone (T−E+) or TGF-β and exudate (T+E+) for 4 days. The assays described previously were used to assess the level of differentiation. Chronic wound exudates decrease the expression of αSMA (mRNA, FIG. 1b). This indicated that chronic wound exudates clearly inhibit fibroblast differentiation. This is correlated to the fact that in chronic wounds, non-functional fibroblasts, also called pseudo-senescent fibroblasts, are present.

Gene Expression Route Upon Fibroblast to Myofibroblast Differentiation

Identification of the main molecular targets implicated in fibroblast differentiation of human primary fibroblasts under normal and pathological conditions The inventors performed an in silico gene network analysis to enlighten putative upstream regulators of the different gene expression routes defined previously. This approach was original in the sense that the inventors used global gene network analysis to identify potential key regulators and the inventors did not take into account a change in these factors expression to select them. For example, the inventors used the DIRE program to identify evolutionary conserved potential regulatory elements in the different genes lists which allowed enlightening transcription factors that could potentially bind to these elements and thus regulate these sets of genes. Twenty-three transcription factors were selected out from this analysis.

To prioritize the extensive study of the different Transcription Factors (TFs), the inventors performed a time response study of TFs after the different fibroblast treatments. The inventors did a short-term (between 30 mn and 8 hours) and a long-term (between 8 hours and 96 hours) analysis of their changes in expression after the different treatments.

The inventors performed an exhaustive siRNA-based approach to study on one hand the role of these different factors in normal fibroblast to myofibroblast differentiation pathway and on the other hand, in the chronic-exudate-dependent non-differentiation cell fate.

The siRNA knock-down of fourteen of the potential key transcription factors identified therein inhibited the fibroblast to myofibroblast differentiation pathway as assessed by analyzing the αSMA expression from TGFβ- and siRNA-treated NHDFs: GLI1, HIC1, TCF4, SOX9, STAT4 MYC, CREB5, IRF7, JUN, E2F1, EGR2, SRF, SMAD3, FOXS1 as their knockdown inhibitor myofibroblast differentiation to various extents (FIG. 2a-b). Very interestingly, except for SOX9, FOXS1 and EGR2, whose expression is strongly and rapidly up-regulated upon TGFβ treatment, the mRNA levels of the other factors is constant during the first day or so after TGFβ treatment and overall unchanged during the four days of differentiation (FIG. 3). This indicates that the maintenance of their expression but not their over-expression is necessary for fibroblast to myofibroblast differentiation.

Figure 5:
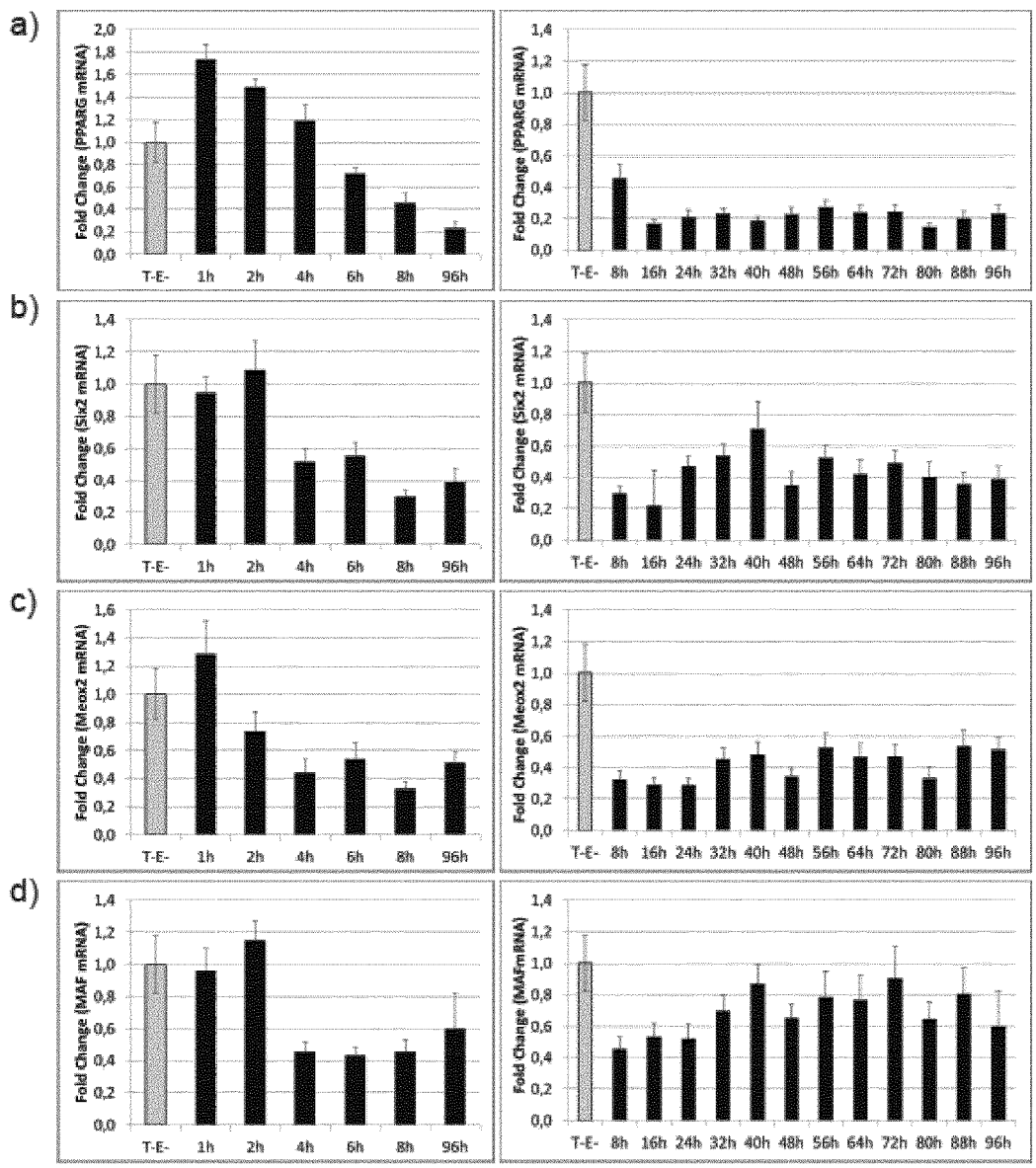
FIG. 5: short and long timing after TGFβ1 treatment for PPARG, MAF, MEOX2 and SIX2. For each Factor, graphic representation of the mRNA levels after increasing time of treatment of the NHDF with TGFβ as assessed by RT-qPCR.

The siRNA knock-down of four other potential key transcription factors identified by the in silico analysis (MAF, SIX2, MEOX2 and PPARG) seemed to induce the fibroblast to myofibroblast differentiation in absence of TGFβ to the same extend as the one obtained with mock transfected cells treated with TGFβ. Even more interestingly the induction of myofibroblast differentiation was old true even in presence of chronic wound exudates and was very similar to the differentiation obtained in presence of TGFβ—only for mock transfected cells. In absence of these factors, the fibroblasts seemed able to bypass the exudate dominant action in order to differentiate into myofibroblasts. The inventors can also enlighten that, except for FOXS1, all these factors are slightly too strongly down regulated upon TGFβ treatment (FIG. 5) supporting that their down regulation could be necessary for differentiation.

Altogether these results showed that with knocking-down approaches the inventors were able either to reduce fibroblast to myofibroblast differentiation or to induce this differentiation even in a chronic wound context (table 1).

An in silico gene network analysis allowed to identify potential key regulators of fibroblast cell fate either during differentiation into myofibroblast or in a context of chronic wounds. By knocking down approaches, the inventors found a strong effect on differentiation for nineteen factors. The strength of our analysis comes from the unbiased approach to look for evolutionary conserved common DNA element in the different lists of genes (via the DIRE program) and from there to identify putative upstream transcription regulators, rather than to look at differences in the expression levels of the transcription factors. It is very likely that the inventors would have missed those cell fate regulators by looking at their differential expression only.

By knocking-down approaches we identified transcription factors required for normal fibroblast to myofibroblast differentiation (FIG. 2). The inventors used the αSMA to follow myofibroblast differentiation as it is their best ex-vivo marker.

The inventors have also identified factors which seemed to play a role but maybe not as strongly as the ones described in the paragraph before as their knockdown leads to consistent but mild decrease of αSMA expression. These factors are MYC, JUN, E2F1, IRF7 and CREB5.

Very interestingly, the inventors showed that the inactivation of some transcription factors leads to an increase of fibroblast differentiation per se. The invalidation of some of these factors could even increase fibroblast to myofibroblast differentiation in a chronic wound context.

The knocking down of PPARG mRNA leads to an increase of fibroblast to myofibroblast differentiation (FIG. 2c-d) even in the presence of chronic exudate.

FOXS1 belongs to the forkhead family of transcription factor often involved in developmental processes such as morphogenesis and differentiation. It has been shown that FOXS1 is of primary importance in the development of testicular vasculature. Moreover, FOXS1 was described as an early sensory neuronal marker. Here the inventors show that inactivation of FOXS1 leads to an increase of myofibroblast differentiation in absence of TGFβ.

MEOX2 has already been described as implicated in TGFβ pathway as it was identified as an important factor in cleft palate development in TGFβ knockout mice. Experiments in C2C12 myoblast cells showed that MEOX2 is also important for skeletal muscle development and differentiation. Here, the inventors showed that siRNA directed against MEOX2 lead to a bypass of the exudate effect by fibroblasts to be able to differentiate into myofibroblasts.

In T cells, it has been shown that MAF was responsible for inhibition of IL22 expression by neutralizing TGFβ. TGFβ and MAF have antagonist/opposite effects on IL21 expression in CD4(+) T cells. In the same connection, in this study, the inventors implicated MAF as an inhibitor of fibroblast to myofibroblast differentiation in absence or presence of exudate as its inactivation by siRNA leads to an increase of myofibroblast differentiation (FIG. 2c-d). On the contrary, during chondrocyte differentiation, a long form of MAF interacts and cooperates with SOX9 to activate downstream targets. This is another example of the differences between myofibroblast and chondrocyte differentiations.

SIX2 has been involved in maintaining pluripotency in kidney: in embryonal renal mesenchyme cells it is able to suppress differentiation and during kidney development it maintains the progenitor pool. Here, in dermal fibroblast, the invalidation of SIX2 leads to a bypass of the dominant exudate effect on TGFβ signaling (FIG. 2c-d).

Figure 6:
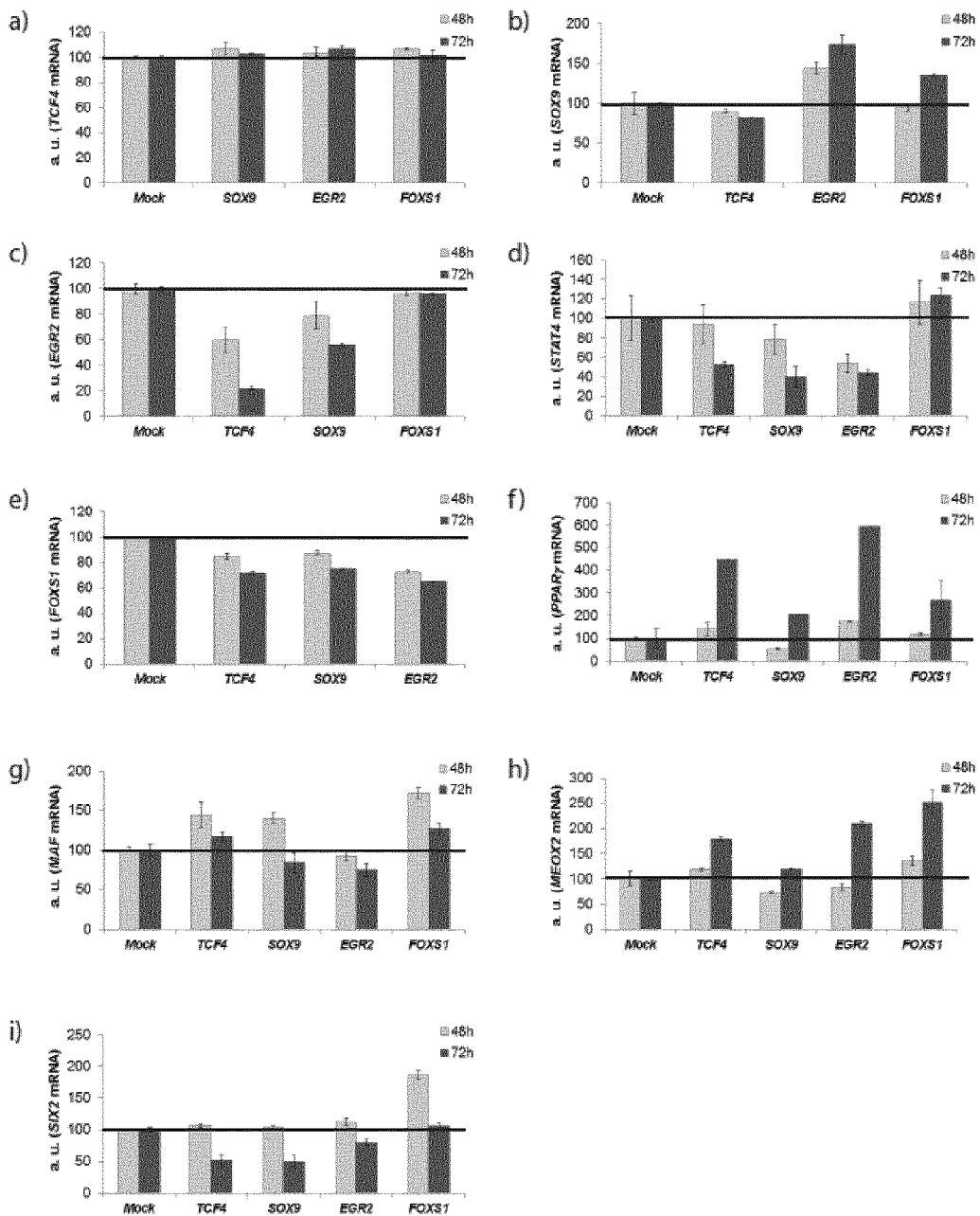
FIG. 6: Graphic representation of the TCF4 (a), EGR2 (b), SOX9 (c), STAT4 (d), FOXS1 (e), PPARG (f), MAF (g), MEOX2 (h), and SIX2 (i) mRNA levels after NHDF (donor A) treatment for 48 h (light grey) or 72 h (dark grey) either with mock siRNA or siRNA directed against different TF mRNA (SOX9, EGR2, TCF4, or FOXS1) and concomitantly treated with TGF-β. For all graphs, the mock siRNA treated with TGF-β (T+E) condition was set to 100% for each time of treatment (48 h and 72 h).

Regulatory Interactions Between Key Transcription Factors During Fibroblast to Myofibroblast Differentiation The expression of TCF4 mRNA was not modified after SOX9, EGR2 or FOXS1 knockdown (FIG. 6) placing it at the top of the regulatory interaction network between these factors. On the contrary EGR2 expression was largely inhibited upon siRNA treatment against TCF4 and SOX9 but remained unchanged upon treatment against FOXS1 (FIG. 6) placing it after TCF4 and SOX9 but before FOXS1 in the network. SOX9 mRNA remained largely unchanged upon TCF4 and FOXS1 knockdown. The inventors placed FOXS1 as a downstream target of SOX9. On the contrary SOX9 is upregulated upon EGR2 knockdown (FIG. 6) The STAT4 mRNA is downregulated by TCF4, SOX9 and EGR2 knockdown (FIG. 6) placing is as a downstream target of those TF whereas it remained unchanged upon FOXS1 siRNA treatment placing it beforehand. Consistently, FOXS1 mRNA is downregulated upon TCF4, SOX9 and EGR2 siRNA treatment (FIG. 6) placing it at the end of this cascade. Globally, the PPARG, MAF and MEOX2 mRNA were upregulated upon siRNA treatment against TCF4, SOX9, EGR2 and FOXS1 (FIG. 6) consistent with their role as antagonist in fibroblast differentiation. SIX2 mRNA level was unchanged upon EGR2 and FOXS1 knockdown (FIG. 6) but upregulated in the same manner by TCF4 and SOX9 consistent with a close interconnection between these two TF and suggesting the existence of a balanced signal between the differentiation agonists SOX9 and TCF4 and the antagonist SIX2.

The identification of transcription factors able to bypass chronic wound exudates effect is of major importance in the chronic wound field as it gives new insight into targets that can be used in the treatment of chronic wounds such as leg ulcers. In this study, by focusing on fibroblast, by no mean the inventors tried to dissimulate the importance of other cells like neutrophils and macrophages in the skin healing process but the inventors willingly simplified the biological context to draw a clearer picture of the situation.

Effects of Drugs on the Fibroblast Differentiation

The inventors have tested several concentrations of drugs to define at least a range of optimal concentrations to observe an effect on the cells: in absence and in presence of TGF-β the inventors expected to observe for some of the drugs either an increase of differentiation or an inhibition of differentiation.

For these tests, the inventors assessed the expression of different genes: αSMA, PI16 (WO2013/144348) and ACTC1 (markers for differentiation, upregulated in myofibroblast cells versus fibroblasts), in presence or not of exsudates.

Trametinib

Figure 8:
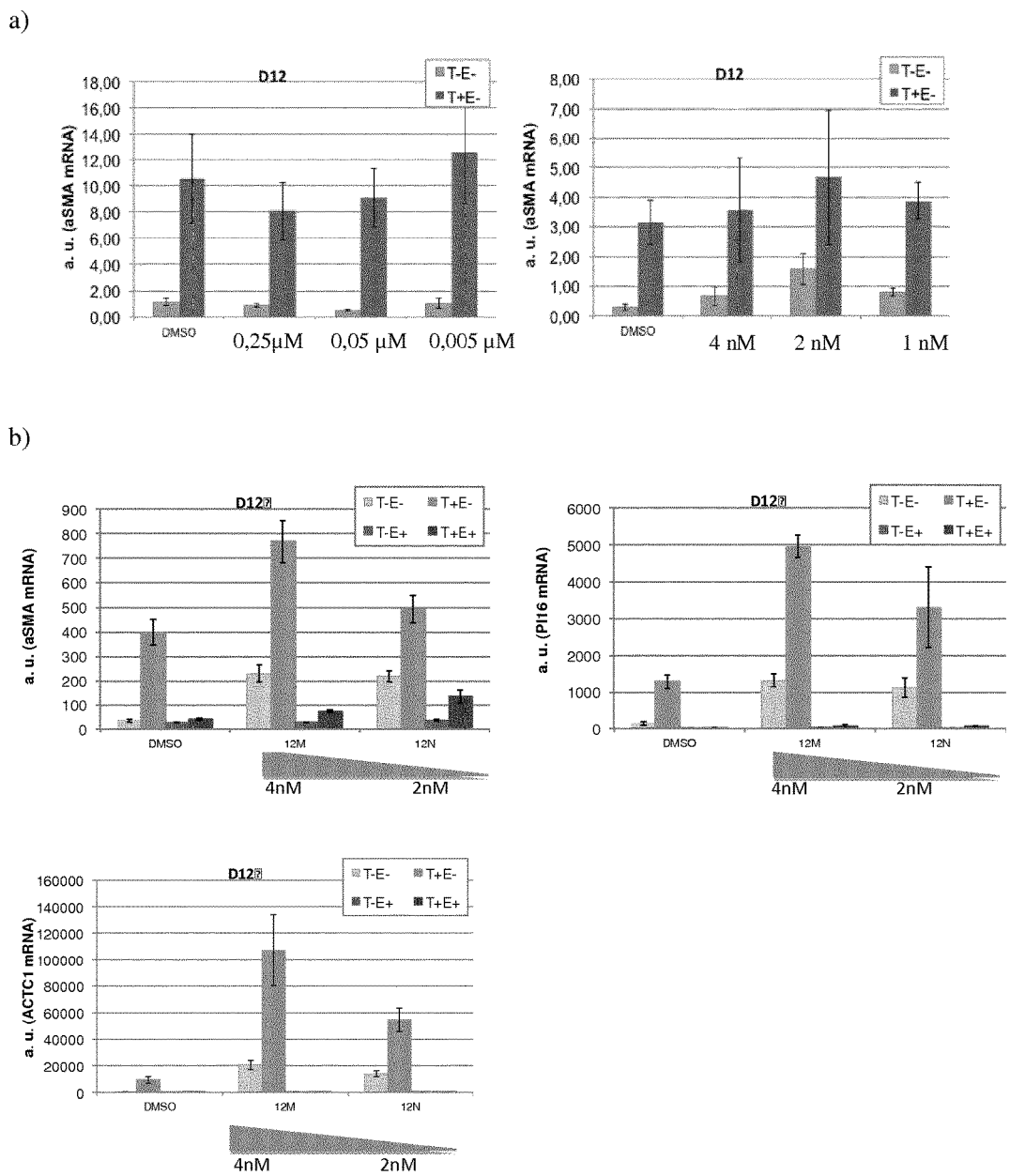
FIG. 8a: Graphic representation of the αSMA mRNA levels as assessed by RT-qPCR of NHDFs treated by Trametinib.
FIG. 8b: Graphic representation of the αSMA, PI16 and ACTC1 mRNA levels as assessed by RT-qPCR of NHDFs treated by Trametinib in the presence of exsudates.

Very interestingly the inventors can see that in presence of Trametinib in between 1 to 4 nM an increase of the basal level of αSMA is observed in non treated fibroblasts (FIG. 8a).

Interestingly Trametinib is able to increase the αSMA myofibroblast marker even in presence of exudate, as well as on PI16 and ACTC1 expression (2 others genes shown to be upregulated upon differentiation) (FIG. 9b). Trametinib might be able to bypass the dominant negative effect of exudate on differentiation and thus could be of great therapeutic interest. Trametinib was described as a MAF antagonist gene so these results are in complete agreement with the siRNA experiments where it was shown that inhibiting MAF expression could launch differentiation.

Am580

Am580 used at 5 nM is able to increase differentiation in presence of TGFβ (FIG. 9a). Am580 is able to potentiate the TGFβ effect on the fibroblast and to increase differentiation as followed with 3 markers upregulated upon differentiation (αSMA, PI16 and ACTC1). Moreover in presence of exudate Am580 is able to erase the negative effect of exudate on differentiation as shown with the increase of αSMA and PI16, in the condition where TGFβbeta, exudate and Am580 were added to the cells, in contrast with the same condition without Am580.

It has been shown that Am580 has an agonist effect on SOX9; these results confirmed the siRNA experiment as it is shown that inhibition of SOX9 (by siRNA treatment) leads to a complete inhibition of differentiation. Here it is shown that treating cells with an agonist of Sox9 gives the opposite effect.

Gant 61

Figure 10:
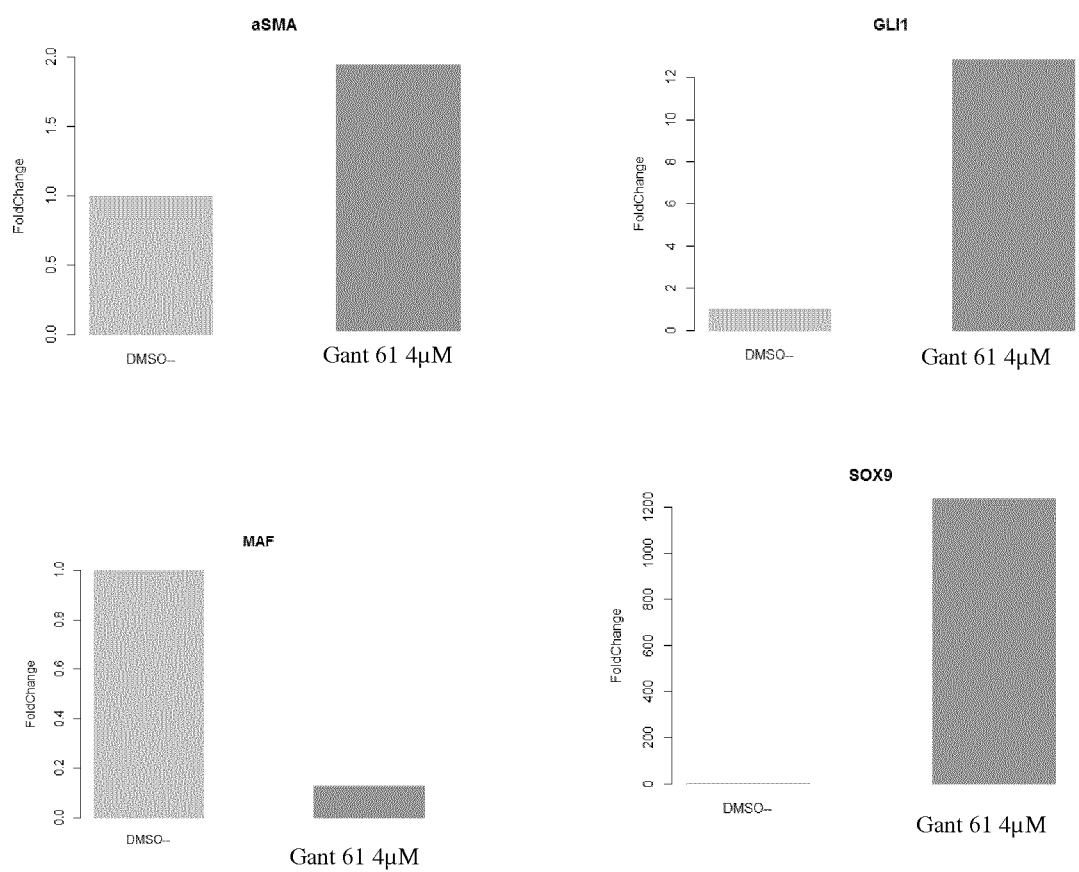
FIG. 10: Graphic representation of the αSMA, GLI1, SOX9 and MAF mRNA levels assessed by RT-qPCR of NHDFs treated by Gant 61.

Gant 61 used at 4 μM is able to increase differentiation as shown by the upregulation of α-SMA (FIG. 10). Surprisingly, Gant 61 is able upregulate the expression of GLI1, however it is reported that Gant 61 is an GLI1 inhibitor (Stanton, Benjamin Z., et al., 2010. Small-molecule modulators of the Sonic Hedgehog signaling pathway. Molecular bioSystems. 6(1): 44-54.) Moreover, Gant 61 induced the increase of SOX9 mRNA and the decrease of MAF mRNA.

The invention claimed is:

1. A method for treating chronic wounds in a subject in need thereof, comprising administering to said subject a therapeutic composition comprising an agent that inhibits expression of a MAF gene, and/or an agent that enhances expression of at least one gene selected from the group consisting of TCF4, FOXS1, or SOX9.

2. The method of claim 1 wherein the agent that inhibits MAF expression comprises an oligonucleotide that is complementary to a MAF RNA and is selected from the group consisting of antisense DNA, antisense RNA, siRNA, shRNA, and ribozyme, or the agent is a vector encoding said oligonucleotide that is complementary to MAF RNA, or the agent is a vector encoding TALENS directed to a MAF gene.

3. The method of claim 1 wherein the composition comprises an agent that inhibits the expression of MAF or an agent that enhances the expression of SOX9.

4. The method of claim 1 wherein the inhibitor of MAF expression is trametinib, and/or the enhancer of SOX9 expression is AM580.

5. The method according to claim 1 wherein it is for treating mammalian chronic wounds.

6. The method according to claim 1 wherein it is for treating chronic wounds selected from the group consisting of venous ulcers, diabetic ulcers, and pressure ulcers.

7. The method according to claim 1 wherein it is for treating human chronic wounds.

8. The method according to claim 1 wherein the therapeutic compound is for topical application.

9. The method according to claim 1 wherein the therapeutic compound is for application to a medical device or impregnation of a medical device.

10. A method for treating chronic wounds in a mammalian subject in need thereof, comprising administering to said subject a therapeutic composition comprising an agent that inhibits the expression or activity of a MAF, and/or an agent that enhances the expression of at least one gene selected from the group consisting of TCF4, FOXS1, or SOX9.

11. The method of claim 1 wherein the therapeutic composition modulates fibroblast and myofibroblast differentiation and/or activity.

12. The method of claim 1 wherein the agent that enhances expression of at least one gene selected from the group consisting of TCF4, FOXS1, and SOX9 is at least one expression vector encoding one or more of TCF4, FOXS1, and SOX9, wherein the vector is in the form of a plasmid or viral vector.

* * * * *

SEQUENCE LISTING

```
<160> NUMBER OF SEQ ID NOS: 74

<210> SEQ ID NO 1
<211> LENGTH: 21
<212> TYPE: RNA
<213> ORGANISM: Artificial Sequence
<220> FEATURE:
<223> OTHER INFORMATION: siRNA

<400> SEQUENCE: 1
uucgaucuga ugaaguuuga a                                                 21

<210> SEQ ID NO 2
<211> LENGTH: 21
<212> TYPE: RNA
<213> ORGANISM: artificial
<220> FEATURE:
<223> OTHER INFORMATION: siRNA

<400> SEQUENCE: 2
cggcaggaga auggcaucag a                                                 21

<210> SEQ ID NO 3
<211> LENGTH: 21
<212> TYPE: RNA
<213> ORGANISM: artificial
<220> FEATURE:
<223> OTHER INFORMATION: siRNA

<400> SEQUENCE: 3
agcaugcgca cuuaugauau a                                                 21

<210> SEQ ID NO 4
<211> LENGTH: 21
<212> TYPE: RNA
<213> ORGANISM: artificial
<220> FEATURE:
<223> OTHER INFORMATION: siRNA

<400> SEQUENCE: 4
cccgcccguc cugugcucca a                                                 21

<210> SEQ ID NO 5
<211> LENGTH: 21
<212> TYPE: RNA
<213> ORGANISM: artificial
<220> FEATURE:
<223> OTHER INFORMATION: siRNA

<400> SEQUENCE: 5
uccggagaac aaucagauug a                                                 21

<210> SEQ ID NO 6
<211> LENGTH: 21
<212> TYPE: RNA
<213> ORGANISM: artificial
<220> FEATURE:
<223> OTHER INFORMATION: siRNA

<400> SEQUENCE: 6
```

```
gagggcgauc uugacaggaa a                                              21

<210> SEQ ID NO 7
<211> LENGTH: 21
<212> TYPE: RNA
<213> ORGANISM: artificial
<220> FEATURE:
<223> OTHER INFORMATION: siRNA

<400> SEQUENCE: 7
caacgagaac uccaauucua a                                              21

<210> SEQ ID NO 8
<211> LENGTH: 21
<212> TYPE: RNA
<213> ORGANISM: artificial
<220> FEATURE:
<223> OTHER INFORMATION: siRNA

<400> SEQUENCE: 8
cccgcugaau ggcagcggca a                                              21

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
ctgttttccc atccattgtg                                                20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
ccatgttcta tcgggtactt                                                20

<210> SEQ ID NO 11
<211> LENGTH: 21
<212> TYPE: RNA
<213> ORGANISM: artificial
<220> FEATURE:
<223> OTHER INFORMATION: siRNA

<400> SEQUENCE: 11
ccggcgaagg gugguagacg a                                              21

<210> SEQ ID NO 12
<211> LENGTH: 21
<212> TYPE: RNA
<213> ORGANISM: artificial
<220> FEATURE:
<223> OTHER INFORMATION: siRNA

<400> SEQUENCE: 12
aacaguauuc uguaggaucu a                                              21

<210> SEQ ID NO 13
<211> LENGTH: 19
<212> TYPE: RNA
```

<213> ORGANISM: artificial
<220> FEATURE:
<223> OTHER INFORMATION: siRNA

<400> SEQUENCE: 13
ucggagaacu uucagaucu                                              19

<210> SEQ ID NO 14
<211> LENGTH: 19
<212> TYPE: RNA
<213> ORGANISM: artificial
<220> FEATURE:
<223> OTHER INFORMATION: siRNA

<400> SEQUENCE: 14
gagaagucac gcuaugaga                                              19

<210> SEQ ID NO 15
<211> LENGTH: 19
<212> TYPE: RNA
<213> ORGANISM: artificial
<220> FEATURE:
<223> OTHER INFORMATION: siRNA

<400> SEQUENCE: 15
gagcagaugg uuaugguga                                              19

<210> SEQ ID NO 16
<211> LENGTH: 19
<212> TYPE: RNA
<213> ORGANISM: artificial
<220> FEATURE:
<223> OTHER INFORMATION: siRNA

<400> SEQUENCE: 16
gaacagggcc acugacucu                                              19

<210> SEQ ID NO 17
<211> LENGTH: 19
<212> TYPE: RNA
<213> ORGANISM: artificial
<220> FEATURE:
<223> OTHER INFORMATION: siRNA

<400> SEQUENCE: 17
gaaggcauaa ucaauauug                                              19

<210> SEQ ID NO 18
<211> LENGTH: 19
<212> TYPE: RNA
<213> ORGANISM: artificial
<220> FEATURE:
<223> OTHER INFORMATION: siRNA

<400> SEQUENCE: 18
cuacuguggc cgaaaguuu                                              19

<210> SEQ ID NO 19
<211> LENGTH: 19
<212> TYPE: RNA
<213> ORGANISM: artificial
<220> FEATURE:
<223> OTHER INFORMATION: siRNA

<400> SEQUENCE: 19
gaaaccagac cuucacuua                                              19

```
<210> SEQ ID NO 20
<211> LENGTH: 19
<212> TYPE: RNA
<213> ORGANISM: artificial
<220> FEATURE:
<223> OTHER INFORMATION: siRNA

<400> SEQUENCE: 20
gagaagaggu cguuggauc                                                    19

<210> SEQ ID NO 21
<211> LENGTH: 21
<212> TYPE: RNA
<213> ORGANISM: artificial
<220> FEATURE:
<223> OTHER INFORMATION: siRNA

<400> SEQUENCE: 21
agggccaaua aagccaugug a                                                 21

<210> SEQ ID NO 22
<211> LENGTH: 21
<212> TYPE: RNA
<213> ORGANISM: artificial
<220> FEATURE:
<223> OTHER INFORMATION: siRNA

<400> SEQUENCE: 22
cuggcucuag gaccugaaga a                                                 21

<210> SEQ ID NO 23
<211> LENGTH: 19
<212> TYPE: RNA
<213> ORGANISM: artificial
<220> FEATURE:
<223> OTHER INFORMATION: siRNA

<400> SEQUENCE: 23
gcaaauaggg cuucacaua                                                    19

<210> SEQ ID NO 24
<211> LENGTH: 19
<212> TYPE: RNA
<213> ORGANISM: artificial
<220> FEATURE:
<223> OTHER INFORMATION: siRNA

<400> SEQUENCE: 24
aggcucagcu uguguguaa                                                    19

<210> SEQ ID NO 25
<211> LENGTH: 19
<212> TYPE: RNA
<213> ORGANISM: artificial
<220> FEATURE:
<223> OTHER INFORMATION: siRNA

<400> SEQUENCE: 25
ggacgaggga ccuugcauu                                                    19

<210> SEQ ID NO 26
<211> LENGTH: 19
<212> TYPE: RNA
<213> ORGANISM: artificial
<220> FEATURE:
```

<223> OTHER INFORMATION: siRNA

<400> SEQUENCE: 26
cagcuagagu ccagagguu                                                    19

<210> SEQ ID NO 27
<211> LENGTH: 19
<212> TYPE: RNA
<213> ORGANISM: artificial
<220> FEATURE:
<223> OTHER INFORMATION: siRNA

<400> SEQUENCE: 27
gcacagcaac gcaaccuca                                                    19

<210> SEQ ID NO 28
<211> LENGTH: 19
<212> TYPE: RNA
<213> ORGANISM: artificial
<220> FEATURE:
<223> OTHER INFORMATION: siRNA

<400> SEQUENCE: 28
gagcuucggu gacaaccug                                                    19

<210> SEQ ID NO 29
<211> LENGTH: 19
<212> TYPE: RNA
<213> ORGANISM: artificial
<220> FEATURE:
<223> OTHER INFORMATION: siRNA

<400> SEQUENCE: 29
ugaucaucgu ggugcagaa                                                    19

<210> SEQ ID NO 30
<211> LENGTH: 19
<212> TYPE: RNA
<213> ORGANISM: artificial
<220> FEATURE:
<223> OTHER INFORMATION: siRNA

<400> SEQUENCE: 30
gaccaucgac cguuucucu                                                    19

<210> SEQ ID NO 31
<211> LENGTH: 19
<212> TYPE: RNA
<213> ORGANISM: artificial
<220> FEATURE:
<223> OTHER INFORMATION: siRNA

<400> SEQUENCE: 31
gcacaaggug uacgcgcuc                                                    19

<210> SEQ ID NO 32
<211> LENGTH: 19
<212> TYPE: RNA
<213> ORGANISM: artificial
<220> FEATURE:
<223> OTHER INFORMATION: siRNA

<400> SEQUENCE: 32
caacuuccgc ugcgcacug                                                    19

```
<210> SEQ ID NO 33
<211> LENGTH: 19
<212> TYPE: RNA
<213> ORGANISM: artificial
<220> FEATURE:
<223> OTHER INFORMATION: siRNA

<400> SEQUENCE: 33
gcgcgcaucu ucaaggccu                                                  19

<210> SEQ ID NO 34
<211> LENGTH: 19
<212> TYPE: RNA
<213> ORGANISM: artificial
<220> FEATURE:
<223> OTHER INFORMATION: siRNA

<400> SEQUENCE: 34
caggcacgga ccagacuga                                                  19

<210> SEQ ID NO 35
<211> LENGTH: 19
<212> TYPE: RNA
<213> ORGANISM: artificial
<220> FEATURE:
<223> OTHER INFORMATION: siRNA

<400> SEQUENCE: 35
gagcggaccu uauggcuac                                                  19

<210> SEQ ID NO 36
<211> LENGTH: 19
<212> TYPE: RNA
<213> ORGANISM: artificial
<220> FEATURE:
<223> OTHER INFORMATION: siRNA

<400> SEQUENCE: 36
gaacaggugg cacagcuua                                                  19

<210> SEQ ID NO 37
<211> LENGTH: 19
<212> TYPE: RNA
<213> ORGANISM: artificial
<220> FEATURE:
<223> OTHER INFORMATION: siRNA

<400> SEQUENCE: 37
gaaacgaccu ucuaugacg                                                  19

<210> SEQ ID NO 38
<211> LENGTH: 19
<212> TYPE: RNA
<213> ORGANISM: artificial
<220> FEATURE:
<223> OTHER INFORMATION: siRNA

<400> SEQUENCE: 38
ugaaagcuca gaacucgga                                                  19

<210> SEQ ID NO 39
<211> LENGTH: 19
<212> TYPE: RNA
<213> ORGANISM: artificial
<220> FEATURE:
<223> OTHER INFORMATION: siRNA
```

<400> SEQUENCE: 39
acggaacucu ugugcguaa        19

<210> SEQ ID NO 40
<211> LENGTH: 19
<212> TYPE: RNA
<213> ORGANISM: artificial
<220> FEATURE:
<223> OTHER INFORMATION: siRNA

<400> SEQUENCE: 40
gaacacacaa cgucuugga        19

<210> SEQ ID NO 41
<211> LENGTH: 19
<212> TYPE: RNA
<213> ORGANISM: artificial
<220> FEATURE:
<223> OTHER INFORMATION: siRNA

<400> SEQUENCE: 41
aacguuagcu ucaccaaca        19

<210> SEQ ID NO 42
<211> LENGTH: 19
<212> TYPE: RNA
<213> ORGANISM: artificial
<220> FEATURE:
<223> OTHER INFORMATION: siRNA

<400> SEQUENCE: 42
cgauguuguu ucuguggaa        19

<210> SEQ ID NO 43
<211> LENGTH: 19
<212> TYPE: RNA
<213> ORGANISM: artificial
<220> FEATURE:
<223> OTHER INFORMATION: siRNA

<400> SEQUENCE: 43
caacaggaau gcagcagug        19

<210> SEQ ID NO 44
<211> LENGTH: 19
<212> TYPE: RNA
<213> ORGANISM: artificial
<220> FEATURE:
<223> OTHER INFORMATION: siRNA

<400> SEQUENCE: 44
gaguucgccu ucaauauga        19

<210> SEQ ID NO 45
<211> LENGTH: 19
<212> TYPE: RNA
<213> ORGANISM: artificial
<220> FEATURE:
<223> OTHER INFORMATION: siRNA

<400> SEQUENCE: 45
ggacgcaggu ucuccaaac        19

<210> SEQ ID NO 46
<211> LENGTH: 19

```
<212> TYPE: RNA
<213> ORGANISM: artificial
<220> FEATURE:
<223> OTHER INFORMATION: siRNA

<400> SEQUENCE: 46
uuagagacau caaguaugg                                                19

<210> SEQ ID NO 47
<211> LENGTH: 19
<212> TYPE: RNA
<213> ORGANISM: artificial
<220> FEATURE:
<223> OTHER INFORMATION: siRNA

<400> SEQUENCE: 47
gcaauugaaa guuugguaa                                                19

<210> SEQ ID NO 48
<211> LENGTH: 19
<212> TYPE: RNA
<213> ORGANISM: artificial
<220> FEATURE:
<223> OTHER INFORMATION: siRNA

<400> SEQUENCE: 48
cccacaaccu uuagacuga                                                19

<210> SEQ ID NO 49
<211> LENGTH: 19
<212> TYPE: RNA
<213> ORGANISM: artificial
<220> FEATURE:
<223> OTHER INFORMATION: siRNA

<400> SEQUENCE: 49
gaauccauau cacuacgaa                                                19

<210> SEQ ID NO 50
<211> LENGTH: 19
<212> TYPE: RNA
<213> ORGANISM: artificial
<220> FEATURE:
<223> OTHER INFORMATION: siRNA

<400> SEQUENCE: 50
guacagaguu acuacuuag                                                19

<210> SEQ ID NO 51
<211> LENGTH: 19
<212> TYPE: RNA
<213> ORGANISM: artificial
<220> FEATURE:
<223> OTHER INFORMATION: siRNA

<400> SEQUENCE: 51
ggaacaaccc gucuacaca                                                19

<210> SEQ ID NO 52
<211> LENGTH: 19
<212> TYPE: RNA
<213> ORGANISM: artificial
<220> FEATURE:
<223> OTHER INFORMATION: siRNA

<400> SEQUENCE: 52
```

| | |
|---|---|
| gaacaagccg cacgucaag | 19 |

<210> SEQ ID NO 53
<211> LENGTH: 19
<212> TYPE: RNA
<213> ORGANISM: artificial
<220> FEATURE:
<223> OTHER INFORMATION: siRNA

<400> SEQUENCE: 53

| | |
|---|---|
| gaccuucgau gucaacgag | 19 |

<210> SEQ ID NO 54
<211> LENGTH: 19
<212> TYPE: RNA
<213> ORGANISM: artificial
<220> FEATURE:
<223> OTHER INFORMATION: sirNA

<400> SEQUENCE: 54

| | |
|---|---|
| ggaagucggu gaagaacgg | 19 |

<210> SEQ ID NO 55
<211> LENGTH: 19
<212> TYPE: RNA
<213> ORGANISM: artificial
<220> FEATURE:
<223> OTHER INFORMATION: siRNA

<400> SEQUENCE: 55

| | |
|---|---|
| ugagacaggc cauguguau | 19 |

<210> SEQ ID NO 56
<211> LENGTH: 19
<212> TYPE: RNA
<213> ORGANISM: artificial
<220> FEATURE:
<223> OTHER INFORMATION: siRNA

<400> SEQUENCE: 56

| | |
|---|---|
| ggacugugcu gaagaguac | 19 |

<210> SEQ ID NO 57
<211> LENGTH: 19
<212> TYPE: RNA
<213> ORGANISM: artificial
<220> FEATURE:
<223> OTHER INFORMATION: siRNA

<400> SEQUENCE: 57

| | |
|---|---|
| gcaccaagag ugaaugauc | 19 |

<210> SEQ ID NO 58
<211> LENGTH: 19
<212> TYPE: RNA
<213> ORGANISM: artificial
<220> FEATURE:
<223> OTHER INFORMATION: siRNA

<400> SEQUENCE: 58

| | |
|---|---|
| gcaccagugu cugcuagug | 19 |

<210> SEQ ID NO 59
<211> LENGTH: 19
<212> TYPE: RNA
<213> ORGANISM: artificial

```
<220> FEATURE:
<223> OTHER INFORMATION: siRNA

<400> SEQUENCE: 59
gcacgauggg cucagcuuu                                                    19

<210> SEQ ID NO 60
<211> LENGTH: 19
<212> TYPE: RNA
<213> ORGANISM: artificial
<220> FEATURE:
<223> OTHER INFORMATION: siRNA

<400> SEQUENCE: 60
cuacgaacau gacccuauc                                                    19

<210> SEQ ID NO 61
<211> LENGTH: 19
<212> TYPE: RNA
<213> ORGANISM: artificial
<220> FEATURE:
<223> OTHER INFORMATION: siRNA

<400> SEQUENCE: 61
gaaccugacu uccaugcgg                                                    19

<210> SEQ ID NO 62
<211> LENGTH: 19
<212> TYPE: RNA
<213> ORGANISM: artificial
<220> FEATURE:
<223> OTHER INFORMATION: siRNA

<400> SEQUENCE: 62
agaaagagcu ugacaguaa                                                    19

<210> SEQ ID NO 63
<211> LENGTH: 19
<212> TYPE: RNA
<213> ORGANISM: artificial
<220> FEATURE:
<223> OTHER INFORMATION: siRNA

<400> SEQUENCE: 63
gaacuaaacu aucagguaa                                                    19

<210> SEQ ID NO 64
<211> LENGTH: 19
<212> TYPE: RNA
<213> ORGANISM: artificial
<220> FEATURE:
<223> OTHER INFORMATION: siRNA

<400> SEQUENCE: 64
gcauguagcu gugguuauu                                                    19

<210> SEQ ID NO 65
<211> LENGTH: 19
<212> TYPE: RNA
<213> ORGANISM: artificial
<220> FEATURE:
<223> OTHER INFORMATION: siRNA

<400> SEQUENCE: 65
caaucuagcu acagugaug                                                    19
```

```
<210> SEQ ID NO 66
<211> LENGTH: 19
<212> TYPE: RNA
<213> ORGANISM: artificial
<220> FEATURE:
<223> OTHER INFORMATION: siRNA

<400> SEQUENCE: 66
cugcgagacu acaaaguua                                                19

<210> SEQ ID NO 67
<211> LENGTH: 19
<212> TYPE: RNA
<213> ORGANISM: artificial
<220> FEATURE:
<223> OTHER INFORMATION: siRNA

<400> SEQUENCE: 67
gcacuugcuu cgaucuauu                                                19

<210> SEQ ID NO 68
<211> LENGTH: 19
<212> TYPE: RNA
<213> ORGANISM: artificial
<220> FEATURE:
<223> OTHER INFORMATION: siRNA

<400> SEQUENCE: 68
gacaaagagc ugagugauu                                                19

<210> SEQ ID NO 69
<211> LENGTH: 19
<212> TYPE: RNA
<213> ORGANISM: artificial
<220> FEATURE:
<223> OTHER INFORMATION: siRNA

<400> SEQUENCE: 69
gcacagcugu uuggucuag                                                19

<210> SEQ ID NO 70
<211> LENGTH: 19
<212> TYPE: RNA
<213> ORGANISM: artificial
<220> FEATURE:
<223> OTHER INFORMATION: siRNA

<400> SEQUENCE: 70
caacgggaca gacaguaua                                                19

<210> SEQ ID NO 71
<211> LENGTH: 19
<212> TYPE: RNA
<213> ORGANISM: artificial
<220> FEATURE:
<223> OTHER INFORMATION: siRNA

<400> SEQUENCE: 71
gcaagacggg agcgaguaa                                                19

<210> SEQ ID NO 72
<211> LENGTH: 19
<212> TYPE: RNA
<213> ORGANISM: artificial
<220> FEATURE:
<223> OTHER INFORMATION: siRNA
```

```
<400> SEQUENCE: 72
ggagggacaa gaucaacaa                                              19

<210> SEQ ID NO 73
<211> LENGTH: 19
<212> TYPE: RNA
<213> ORGANISM: artificial
<220> FEATURE:
<223> OTHER INFORMATION: siRNA

<400> SEQUENCE: 73
gaagagccca gcacaacga                                              19

<210> SEQ ID NO 74
<211> LENGTH: 19
<212> TYPE: RNA
<213> ORGANISM: artificial
<220> FEATURE:
<223> OTHER INFORMATION: siRNA

<400> SEQUENCE: 74
caaaaucccu ucagcaaug                                              19
```